United States Patent [19]

Manahan, Sr.

[11] Patent Number: 5,770,791
[45] Date of Patent: Jun. 23, 1998

[54] METHOD AND APPARATUS FOR ACCURATE MEASUREMENT OF IMPACT FRACTURE BEHAVIOR

[76] Inventor: Michael Peter Manahan, Sr., 2274 Oak Leaf Dr., State College, Pa. 16803

[21] Appl. No.: 663,917

[22] Filed: Jun. 14, 1996

[51] Int. Cl.$^6$ .............................. G01H 7/00; G01N 3/30; G01N 3/32
[52] U.S. Cl. ............................................. 73/12.01; 73/82
[58] Field of Search .............................. 73/12.01, 12.04, 73/12.05, 12.06, 12.07, 12.09, 12.13, 12.14, 82, 83, 84, 85

[56] References Cited

U.S. PATENT DOCUMENTS

| | | | |
|---|---|---|---|
| 4,168,620 | 9/1979 | Schrader | 73/12.09 |
| 4,405,243 | 9/1983 | Kuraoka et al. | 73/12.13 |
| 4,546,654 | 10/1985 | Isherwood et al. | 73/12.09 |
| 4,567,774 | 2/1986 | Manahan | 73/826 |
| 4,864,867 | 9/1989 | Manahan | 73/851 |
| 5,165,287 | 11/1992 | Manahan | 73/851 |

OTHER PUBLICATIONS

ASTM Draft Standard, "Proposed ASTM Standard Method for Instrumented Charpy V–Notch and Miniaturized Charpy V–Notch Impact Tests on Metallic Materials", 1996, Entire Document.
Lucas et. al., "Subsized Bend and Charpy V–Notch Specimens for Irradiated Testing", 1986, pp. 307–310.
Corwin et. al., "Effect of Specimen Size and Material Condition on the Charpy Impact Properties of 9Cr–1Mo–V–Nb Steel", 1986, pp. 332–334.
Manahan, "Miniaturized Charpy Test Optimization for Applications in the Power Industry", Jun., 1995, Entire Report.
ASTM Standard E23–93a, "Standard Test Methods for Notched Bar Impact Testing of Metallic Materials", 1993, pp. 206–219.
Nanstad et al., "Influence of Thermal Conditioning Media on Charpy Specimen Test Temperature", 1990, pp. 195–198.
Kumar et al., "Recent Improvements in Size Effects Correlations for DBTT and Upper Shelf Energy of Ferritic Steels", 1993, pp. 47–59.
Manahan et al., "A Generalized Methodology for Obtaining Quantitative Charpy Data from Test Specimens of Now Standard Dimensions", 1989, pp. 247–256.

*Primary Examiner*—George M. Dombroske
*Assistant Examiner*—Max H. Noori

[57] ABSTRACT

Methods and apparatus for the accurate determination of impact fracture behavior of materials. Test specimens are thermally preconditioned in-situ by flowing a thermally conditioned gas over the surfaces of the specimen which contain the volume of material near the notch and/or pre-crack which influences the fracture properties. Upper shelf energy is determined using miniature specimens which is quantitatively equivalent to the upper shelf energy which would have been obtained using conventional ASTM E 23 specimens. Percent shear fracture area and lateral expansion are measured using a computerized image capture system to reproduce a digitized image of the fracture surface on a computer which is then quantitatively analyzed. A high frequency response load cell, consisting in part of two active strain gages installed near the center of percussion on the tapered portion of an impact striker, well within one stress wavelength of the striking surface, is used to measure the force-time curve. Balancing resistors are used to complete a Wheatstone bride circuit and these balancing resistors are not mounted on the striker to avoid sensing reflected stress waves. The instrumented striker is calibrated after it is installed in the test machine by placing a calibrated load cell and a hydraulic jack within a load reaction frame which surrounds the instrumented striker, calibrated load cell, and hydraulic jack.

8 Claims, 23 Drawing Sheets

Conventional Charpy Specimens
As-received Material

Conventional Charpy Specimens
Simulated Irradiated Material

Miniature Sidegrooved Specimens
As-received Material

Miniature Sidegrooved Specimens
Simulated Irradiated Material $E_I$ = exitation voltage $E_o$ = output voltage

METHOD AND APPARATUS FOR ACCURATE MEASUREMENT OF IMPACT FRACTURE BEHAVIOR

BACKGROUND

1. Field of the Invention

This invention relates to methods and apparatus for impact tests of notched and pre-cracked specimens to determine the fracture behavior of materials. The current impact testing art involves thermal pre-conditioning of the specimen in a bath or furnace prior to impact loading and requires rapid physical transfer of the specimen to the test fixture. This invention eliminates the need for transfer of the specimen to the test fixture which reduces data scatter due to temperature variation and misalignment and is especially useful for testing miniature specimens where specimen transfer without large temperature variations is virtually impossible. This invention also provides a means for accurate measurement of percent shear fracture area, lateral expansion, upper shelf energy, and characteristic load data. The invention is especially useful for the purpose of establishing the design, use, and safe life criteria of the material.

In many applications, the method must be employed in conjunction with miniature specimens to accommodate constraints associated with limited volume of material. Although the term "miniature" is relative, as are all size descriptive terms, it is a fair characterization to define the field of this invention as impact testing using conventionally sized or miniaturized specimens, and with miniature meaning noticeably smaller than previously used in the conventional test method.

2. Description of Prior Art

Determination of the mechanical, physical, and fracture properties of materials is necessary so that materials may be selected for use, evaluated when in use, and evaluated after use. From these determinations, decisions are made as to which materials to use, the conditions under which they can be used, and whether such materials in use can be continued to be used with safety. These types of determinations are particularly useful for evaluating the effects of environmental loading such as nuclear radiation, temperature, water chemistry, and force (load) on the mechanical properties of in-service materials.

While not limited to the field of determining the effects of nuclear irradiation and environment on the mechanical properties of materials, the impetus for the invention originated with the needs and necessities of this activity. The invention is fully applicable to the determination of mechanical behavior of materials not subjected to radiation, and the validity of the invention was demonstrated for materials not subjected to radiation. Within the nuclear industry, a limited number of surveillance capsules (typically 3, 4 or 5 capsules) containing Charpy V-notch specimens (also referred to in the literature as Charpy specimens after the original developer of the test) have been installed during construction of the plant near the inner diameter surface of the reactor pressure vessel (RPV) for the purpose of providing data throughout the useful life of the plant. Over the past ten years, it has been discovered that the phenomenology of radiation damage in RPV steels is more complex than originally thought and the amount of damage in some plants is higher than considered safe by regulatory bodies and these plants will have to undergo a vessel thermal annealing to continue safe operation. Accordingly, there is an ever increasing need for more fracture data, and the use of miniature specimens, which can be machined from the broken halves of previously tested conventional Charpy specimens, offers an effective solution to this problem. A similar need exists in other fields, such as the fossil power industry, where exposure of piping and other components to high temperatures causes thermal aging and damage to the material. It is preferred that only small pieces of material be removed from the in-service components and fracture test data are needed for the service damaged material.

The prior art includes U.S. Pat. Nos. 4,567,774 (1), 4,864,867 (2), and 5,165,287 (3) having the inventor, Michael P. Manahan, Sr., common with this application. These earlier patents, hereinafter referred to as the "prior patents", include the basic concepts and apparatus upon which the miniature specimen portions of this invention is based. The disclosure of the prior patents is included herein by reference and the portions of that disclosure not specifically needed for the disclosure of this improvement invention are not included herein. However, reference to the prior patents may be helpful to the understanding hereof.

This invention is described in part in a report entitled, "Miniaturized Charpy Test Optimization for Applications in the Power Industry", by Michael P. Manahan, Sr. (the applicant herein),—prepared for The Empire State Electric Energy Research Corporation (ESEERCO), Jun. 21, 1995 (4). The reference (4) disclosure is included herein.

Specimen Thermal Conditioning

In the current test practice, specimens are heated (or cooled) in a liquid or gaseous medium which is in close proximity to the impact test machine, and after the desired temperature is reached and maintained for a short time, the specimen is transferred to the specimen supports (positioned against the anvils) using precision centering tongs or a robotic transfer machine. The American Society for Testing and Materials (ASTM) Charpy test procedure, which is described in standard E 23 (5), may be summarized as follows: the specimen is heated (or cooled) in a separate container using a liquid or gas medium; the test specimen is removed from its heating (or cooling) medium and positioned on the specimen supports manually using precision centering tongs or automatically using a robotic transfer machine; the specimen is positioned so that the notch, or precrack, is centered between the anvils with the notch face against the anvils; the pendulum, which contains the striker, must then be released (without vibration) and strike the specimen within 5 seconds after removal from the medium (for conventional specimens); and at least one key variable is measured such as absorbed energy, applied load, and/or specimen deflection. The ASTM standard E-23 requires that the specimen be struck within 5 seconds to ensure that the change in temperature resulting from the transfer to the specimen support is negligible, and this requirement only applies to the conventional Charpy specimens. Five seconds is much too long for miniature specimens because of large temperature variations (reference 4).

The current Charpy test procedure involves transfer of a thermally preconditioned specimen to the specimen supports/anvils because it is not obvious how it would be possible to thermally condition the specimen on the supports and simultaneously allow for the impact of the striker with the specimen to occur. The fact that in-situ thermal conditioning of impact test specimens is not obvious is demonstrated by the fact that those highly skilled in the practice of the Charpy test have spent large sums of money to develop robotic transfer machines to move the test specimen rapidly to the anvils from the thermal conditioning medium. A typical robotic transfer machine was developed by Oak Ridge National Laboratory and is described in reference (6).

The disadvantages of the current practice for heating or cooling specimens include: the variation of the temperature introduces scatter in the data because the fracture properties of most material depend strongly on test temperature; the variation of centering of the specimen on the anvils introduces scatter in the data because the stresses in the specimen which lead to fracture depend strongly on precision of the notch, or precrack, centering between the anvils (reference (5) requires that the center of the notch be located within 0.25 mm of the midpoint between the anvils); manual transfer using tongs, as recommended in reference (5), can result in the impact test being performed on a specimen which is inadvertently misaligned by more that 0.25 mm due to "bumping" the specimen with the tongs as the specimen is released on the anvils; and the cost to develop or purchase a robotic transfer system is high and this cost can be averted by the present invention.

As a result of the specimen size, handling and alignment of miniature notched bar or precracked bar specimens is virtually impossible using centering tongs. Because of the reduced mass, the time for transfer of miniature specimens from the thermal conditioning medium must be significantly reduced. Miniature and conventional specimens were instrumented with internal and surface thermocouples and the temperature was measured as a function of time after removal from a liquid bath (4). The temperature variation of the miniature specimens after 5 seconds was found to be unacceptably large. Since it is very difficult to transfer and strike a conventional Charpy specimen in under 4 seconds, manual specimen transfer is not an acceptable method for use with miniature specimens. While it is recognized that a robotic transfer approach could be used, it is very difficult to transfer and strike a miniature specimen in under 2 seconds with such an automated system, and even if this could be done reliably, there would still be a temperature and alignment uncertainty. Further, it is difficult to ensure alignment accuracy and reliability using robotic systems. Accordingly, an in-situ heating (or cooling) system has been invented to solve this problem. This approach has the inherent advantage that the specimen can be aligned to very high accuracy prior to starting the in-situ heating and/or cooling process. Another advantage is that the specimen is continuously thermally conditioned up to the instant of strike. Reduction of variability in these two critical experimental variables has substantially improved the quality of the fracture behavior data which is measured.

Determination of Upper Shelf Energy Using Miniature Specimens

The current test procedures (5) involve the measurement of the total energy absorbed by the specimen as a result of the impact and this measurement is made using a machine with graduated scales in degrees or, more directly, in energy. Since miniature specimens can have total absorbed energy levels which are on the order of 10 times lower than conventional specimens, the use of a scale with graduations in energy is not sufficiently accurate in the low energy range of miniature specimens. It is preferable to use a high accuracy optical encoder to measure the total absorbed energy of a miniature specimen. An alternative approach is to measure the applied force as a function of time during the impact of the striker with the specimen, by instrumenting the striker with strain gages, and then perform a double integration to obtain the force-displacement relationship. Integration of the force-displacement relationship gives an alternative and accurate measure of the energy absorbed by the specimen. Characteristic values (7) of force, displacement, and energy can be defined which correspond to the general yield load, the maximum load, the brittle fracture initiation load, and the brittle fracture arrest load. Instrumented impact data reported in the literature require very large calibration factors (typically 30% to a factor of 2) to convert the measured load cell voltage to force. Another problem with literature data is the fact that the force-time response curve does not accurately represent the actual response. Because the current approach involves attaching all of the Wheatstone bridge strain gages to the striker and/or pendulum, the voltage signals of interest are distorted by reflected stress waves. Further discussion on instrumented testing follows.

As described in references (1–4), the problem of obtaining transitional fracture data without significant energy-temperature downward shifts has been solved by fabricating miniature specimens with sidegrooves. However, the magnitude of the energies measured using miniature specimens are significantly lower than for conventional specimens. Therefore, a scaling factor of general applicability is needed to provide quantitative upper shelf energy (USE) data from miniaturized Charpy V-Notch (MCVN) specimens which is equivalent to that obtained using conventional ASTM E 23 specimens. Other researchers have attempted to formulate correlations for non-sidegrooved specimens. However, none of these correlations have been successful over wide ductility ranges. These prior efforts were mainly focused on correlating high ductility (USE~200 J) materials. Lucas et. al. (8) used an approximate specimen dimension normalization in the form of $Bb^2$, where B is the specimen width and b is the initial ligament. Corwin et. al. (9) proposed a alternative volume normalization of the form $(Bb)^{3/2}$. However, neither of these correlations were successful in the low ductility (USE~100 J) range. Kumar originally developed a correlation for low ductility steels which were being studied in the national fusion alloy development program, but it was later found that this correlation does not work well for the high ductility materials. More recently, Kumar et. al. (10) have followed the energy partitioning theory of reference (11) and developed a correlation based on the ratio of the measured post-maximum load energy to the fracture volume for the miniature and conventional specimens. While the energy partitioning approach to data analysis is valid, the reference (10) method is unnecessarily complicated and lacks a sound theoretical basis, and is not expected to yield valid results for all materials.

The correct approach is to use sidegrooved specimens which closely simulate the stress field present in the conventional Charpy V-Notch (CVN) specimens. If the stress fields in the miniature specimen reasonably simulates those in the CVN specimen, then a fracture process volume (FPV) normalization can be applied directly to the miniature specimen data. The reason why the earlier attempts described above were met with limited success is because the stress fields in the non-sidegrooved specimens did not closely simulate the conventional specimen stress field, the fracture volume normalization was not accurate, and the fracture volume was not corrected for the ductility of the material being tested. The key to the solution of this problem is related to the discovery that when the stress field in the miniature specimen closely simulates that of the conventional specimen, then the energy required to initiate the crack at the root of the notch is ~⅓ of the total energy in both the CVN and MCVN specimens. This initiation energy proportionality is independent of the ductility of the material. Therefore, the pre-maximum load energy, or the energy up to crack formation along the length of the root of the notch, is proportional to the total energy absorbed by the specimen, and finite element calculations or characteristic load data can be used to correct the fracture volume to account for differing ductilities which result from the CVN and MCVN size differences.

Determination of Percent Shear Fracture Area and Lateral Expansion

The current test procedures (5) also include methods for measurement of the percentage (%) of shear fracture area and lateral expansion which result from the dynamic fracture event. At present, within the nuclear industry, % shear fracture area is not widely used and is rarely measured. This is due in part to the difficulty involved in accurate measurement of % shear. ASTM E 23 (5) offers four methods for measurement of % shear: measure the length and width of the cleavage portion of the fracture and use tabulated data to determine % shear; compare with a fracture appearance chart which increases in 10% shear increments; magnify the fracture surface and compare it to a precalibrated overlay chart; and photograph the fracture surface and measure using a planimeter. The accuracy of the former three methods is poor. The latter method has good accuracy, but the technique is tedious. Lateral expansion is currently measured using a lateral expansion gage (5). The use of existing lateral expansion gages does not work with MCVN specimens because of the small size of the MCVN specimens. While it may be feasible to design a miniature specimen lateral expansion gage, such a gage will not work with sidegrooved specimens. A solution to the problem of measuring % shear and lateral expansion has been solved by using an image analysis system to capture the image of the fracture surface on computer and to use on-screen digital measuring software to determine the MCVN % shear and lateral expansion. This approach has the inherent advantage of lowering dose rates to the personnel because the imaging can be done remotely behind shield walls.

Measurement of Characteristic Load Data

Attaching strain gages to the striker enables measurement of the force-time relationship during loading of the specimen to fracture in an impact test. The current approach involves attaching strain gages to the striker to form a full Wheatstone bridge. A variety of load cell designs have been reported in the literature, but all involve full bridges with four resistors mounted on the striker and/or pendulum. Many laboratories include electronic filters to suppress the load oscillations associated with the dynamic impact response. Calibration is usually performed by determining the total energy absorbed by integrating the load-time curve, comparing with the machine dial or optical encoder energy, and determining by ratio the correction factor which gives the correct absorbed energy from the instrumented striker. Another calibration procedure is to clamp the striker between two flat plates in a tensile testing machine and comparing the instrumented striker output voltage with the calibrated load cell output. Both of these methods are not satisfactory because the correction factors are often very large (~ of 30% to as high as a factor of 2) and can vary with the material being tested. Other problems and disadvantages associated with the prior art include: force-time curves do not accurately represent actual behavior; the instrumented system response is too slow to capture high frequency events such as brittle fracture and initial acceleration of the specimen at impact; the active strain gages are not mounted close enough to the impact location which results in measurement of fictitious inertial forces; and force-time curves are distorted by reflected stress waves because the bridge completion resistors are mounted on the striker and/or pendulum.

OBJECTS AND ADVANTAGES

Accordingly, several objects and advantages of my invention are:

(a) to provide a method and apparatus for thermally conditioning a fracture behavior specimen in-situ prior to impact testing, after it has been accurately aligned on the test machine anvils, which has the benefit of decreasing data scatter due to misalignment and temperature change which occurs in the current test method (which requires transfer to the specimen supports (against the anvils) from a separate bath or oven);

(b) to provide a method and apparatus for thermally conditioning a miniature fracture behavior specimen in-situ prior to impact testing, after it has been accurately aligned on the test machine machine supports against anvils, which enables accurate testing of miniature specimens and to decreases unacceptably large data scatter due to misalignment and temperature change which occurs in the transfer to the test machine from a separate bath or oven;

(c) to provide a method and apparatus for thermally conditioning impact (dynamic) fracture test specimens which does not require costly robotic transfer systems;

(d) to provide a method and apparatus for thermally conditioning dynamic fracture test specimens which does not cause mistests to occur as a result of inadvertently "bumping" the specimen with tongs as the specimen is released on the anvils as occurs with the current test practice;

(e) to provide a means for reliably converting the USE measured using miniature specimens to a value which is equivalent to that which would be obtained if conventional Charpy specimens had been tested;

(f) to provide a means for accurately measuring the percent shear fracture area after a fracture test using imaging and quantitative image analysis to give results which are more accurate, and less costly, as compared with current methods;

(g) to provide a means for accurately measuring the lateral expansion after a fracture test using imaging and quantitative image analysis to give results which are more accurate, and less costly, as compared with current methods;

(h) to provide a means for measuring the load-time response during impact testing which enables accurate determination of the characteristic load, deflection, and energy values;

(i) to provide a means for accurately calibrating an instrumented striker which has the benefit of enabling measurement of characteristic load, deflection, and energy data; and (j) to provide a means for measuring force accurately during impact testing which minimizes or eliminates fictitious inertial forces.

Further objects and advantages of my invention will become apparent from a consideration of the drawings and ensuing description.

SUMMARY OF THE INVENTION

In summary, the method and apparatus for accurate measurement of impact fracture behavior is:

1. A method for thermally conditioning a specimen (125) in-situ prior to performing an impact test, comprising the steps of:

a. positioning said specimen in a test fixture (126,128);

b. thermally conditioning said specimen by flowing a thermally conditioned fluid over surfaces of said specimen;

c. impacting said specimen; and d. measuring at least one key variable in step c. such as absorbed energy, applied load, and/or specimen deflection;

whereby said specimen will be impact tested with an accurate alignment at a known temperature.

2. An apparatus for providing thermal conditioning of a fracture behavior test specimen (125) prior to performing an impact test, comprising:

a. a pressurized fluid capable of flowing through a duct;

b. a heater and/or refrigerator capable of thermally conditioning said fluid; and c. means for flowing said thermally conditioned fluid over surfaces (137,138,139,140) of said fracture test specimen which is fixtured in an impact test machine prior to impact testing;

whereby said specimen will be impact tested with an accurate alignment at a known temperature.

3. A method for determining conventional Charpy V-notch upper shelf energy of a material using a miniature specimen, comprising the steps of:

a. impact testing said miniature specimen at a temperature which yields entirely ductile fracture;

b. measuring total absorbed energy in step a., c. calculating a fracture process volume for a Charpy V-notch specimen and for said miniature specimen;

d. calculating a ratio of the Charpy V-notch specimen fracture process volume to the miniature specimen fracture process volume;

e. determining a plastic zone correction factor which relates the miniature specimen fracture process volume to the Charpy specimen fracture process volume; and f. calculating substantially equivalent Charpy V-notch upper shelf energy by multiplying energy measured in step b. by the fracture process volume ratio calculated in step d. and multiplying the result by the plastic zone correction factor determined in step e., whereby an upper shelf energy will be determined using miniature specimens which is substantially equivalent to the upper shelf energy which would be obtained by testing conventional Charpy V-notch specimens at a temperature which yields entirely ductile fracture.

4. A method for measuring percent shear fracture area of a fracture behavior specimen, comprising the steps of:

a. capturing a digitized image of said fracture behavior specimen fracture surface on a computer;

b. outlining brittle fracture region and total fracture region of said fracture surface;

c. using computer program to calculate the area of said regions of step b.; and d. calculating percent shear fracture area and/or percent brittle fracture area using said areas of step d.;

whereby an accurate and reproducible measurement of the percent shear and/or percent brittle fracture area of a fracture behavior test specimen is made.

5. A method for measuring lateral expansion of a fracture behavior specimen, comprising the steps of:

a. capturing a digitized image of said fracture behavior specimen fracture surface on a computer;

b. marking said digitized image of step a. to define the extent to which the lateral expansion has occurred on said fracture behavior specimen; and c. measuring the distance between said marks of step b. in a direction which is substantially normal to the direction of crack propagation and substantially in the direction of lateral expansion material flow;

whereby and accurate and reproducible measurement of the lateral expansion which occurs during fracture is made.

6. A method for measuring force during impact testing, comprising the steps of:

a. attaching active strain gages (454,456) to a striker (127);

b. locating said active stain gages of step a. well within one stress wavelength of striking surface; and c. completing load cell circuit by locating balancing resistors (458,459) away from striker where stress waves from impact test cannot be sensed.

7. A method for calibrating an instrumented striker, comprising the steps of:

a. positioning said instrumented striker between two flat plates (504,506) in a tensile machine load train which contains a calibrated load cell (606);

b. placing a specimen of substantially same dimensions as will be impact tested using said instrumented striker between instrumented striker and one of said flat plates of step a.;

c. aligning said instrumented striker and said specimen of step b. such that specimen is in contact with said instrumented striker in said tensile machine load train in substantially the same position and orientation as in an impact test machine which will be used for impact testing;

d. applying static loads to said instrumented striker and said calibrated load cell to determine the relationship between instrumented striker voltage output and applied force.

8. A method for calibrating an instrumented striker which is installed in an impact test machine, comprising the steps of:

a. placing a specimen of substantially same dimensions as specimens to be impact tested on said impact test machine specimen supports against anvils;

b. positioning said test machine striker in contact with said specimen of step a.;

c. placing an expandable member (602) against test machine anvils;

d. surrounding said instrumented striker and said expandable member with a force reaction frame (608,610,612, 614) which contains a calibrated load cell (606);

e. applying displacements using said expandable member such that said force reaction frame applies a load to instrumented striker and to said calibrated load cell;

f. recording at least one output voltage from said instrumented striker and from said calibrated load cell to relate instrumented striker output voltage to applied force.

9. An apparatus for calibrating an instrumented striker which is installed in an impact test machine, comprising:

a. a calibrated load cell (606) and an expandable member (602);

b. a force reaction frame (608,610,612,614) of sufficient size to surround said instrumented striker, said calibrated load cell, and said expandable member;

c. means for applying displacements using said expandable member such that a load is applied simultaneously to said calibrated load cell and said instrumented striker.

In summary, this invention is a method and apparatus for accurately determining the impact, or dynamic, fracture behavior of materials. The elements of a typical test include: (a) providing a conventional Charpy specimen or miniature bar, which may be notched, and/or sidegrooved, and/or precracked; (b) providing a pendulum or drop tower test machine with a striker, supports, and anvils, capable of impact loading the specimen; (c) aligning the specimen in the test machine, prior to heating and/or cooling the specimen, such that the specimen notch and/or precrack is located in the center of the span between the anvils and opposite the side to be struck by the test machine striker; (d) heating and/or cooling the specimen in-situ using a flow of temperature conditioned and, if desired, humidity controlled, gas (or a liquid) which is directed to flow around the outside surfaces of the specimen which is situated on the specimen supports against the anvils; (e) providing temperature measurement instrumentation to measure the specimen temperature and/or the flowing gas temperature; (f) impact testing the specimen to produce a fracture in the specimen after the desired temperature is reached; and (e) measuring at least one key variable if step (f).

This invention is directed to solving the problem of temperature variation within the specimen when transferring the specimen from a separate thermal conditioning medium to the specimen support against the anvil surfaces and then impacting the specimen as soon as possible after the specimen is positioned in the test machine. The invention enables the specimen to be continuously heated and/or cooled up to the instant of striker impact. The invention solves the problem of significant thermal losses associated with transfer from a separate thermal conditioning medium. The invention also enables very accurate specimen alignment on the anvils because the alignment can be performed using precision measurement equipment, such as high accuracy digital micrometers and precision tongs, prior to heating or cooling of the specimen. The invention reduces uncertainty inherent in the current test practice by decreasing the temperature variation of the specimen which is thermally conditioned in-situ and by decreasing the misalignment uncertainty. Another advantage of the invention is that the number of mistests due to misalignment is reduced and may be eliminated because the operator need not run the test if there is reason to believe that the specimen is not correctly aligned. This is particularity important in cases where only a limited volume of material is available.

Another object of this invention is the determination of the USE, which is equivalent in magnitude to the USE measured using conventional CVN specimens, using MCVN specimens. This is very valuable information for nuclear power plants because many plants have low USE levels which have, or will, exceed the NRC screening criterion level of 50 ft.-lbs. Many plants have, or will, use up all of their full size Charpy specimens and will require some means for measuring USE. Miniature specimens, which can be machined from conventional specimen broken halves, offer a solution to this problem if a MCVN USE conversion factor can be obtained. This invention provides the method for obtaining the conversion factor.

Another object of this invention is the accurate determination of % shear and lateral expansion. Currently available devices for measuring lateral expansion in CVN specimens are not sufficiently accurate for use with miniaturized specimens and will not work at all with sidegrooved specimens. The current methods for measuring % shear are tedious and inaccurate. The invention provides a method for using computer imaging and quantitative analysis to determine the % shear and lateral expansion with high accuracy for conventional CVN and MCVN specimens with and without sidegrooves.

Another object of this invention is to provide a means for measuring the load-time response during impact testing which enables accurate determination of the characteristic load, deflection, and energy values and to provide a means for accurately calibrating an instrumented striker.

The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art, without departing from the scope or sacrificing any of the advantages of the invention.

REFERENCE NUMERALS IN DRAWINGS

Figure 1:
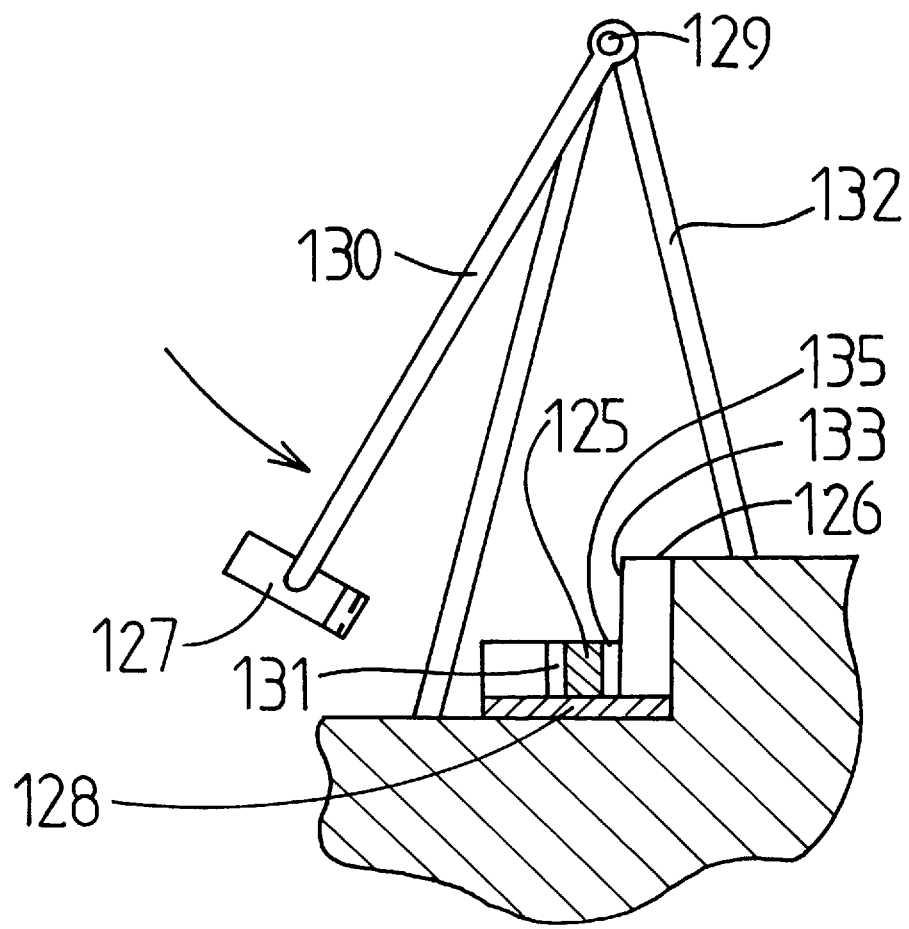
FIG. 1 is a schematic elevational view of one of the fixtures and specimens employed in the standard ASTM standard E 23 impact (Charpy) test used to determine the dynamic properties of materials.

| REFERENCE NUMERALS IN DRAWINGS | | | |
|---|---|---|---|
| 125 | specimen | 126 | anvils |
| 127 | striker | 128 | specimen supports |
| 129 | trunnion axis | 130 | pendulum arm |
| 131 | specimen receptacle | 132 | rigid pendulum arm support |
| 133 | anvil ledge faces | 134 | rigid test machine base |
| 135 | specimen notch | 137 | notched surface of specimen |
| 138 | impact surface of specimen | 139 | specimen side normal to notched side opposite side 140 |
| 140 | specimen side normal to notched side which rests on 128 | 141 | square end of specimen |
| 142 | square end of specimen | 150 | centering tongs |
| 151 | specimen holding piece | 152 | notch centering piece which passes between anvils |
| 155 | thermal conditioning apparatus with temperature control and agitation | 156 | agitated liquid bath |
| 158 | raised grid to keep specimen within agitated liquid region | 202 | thermally conditioned gas delivery duct |
| 204 | gas temperature control thermocouple | 206 | gas temperature controller |

-continued

| REFERENCE NUMERALS IN DRAWINGS | | | |
|---|---|---|---|
| 208 | gas heating unit | 210 | gas refrigeration unit |
| 212 | gas shutoff valves | 214 | compressed air supply ducts |
| 216 | air dryer unit | 218 | gas reservoir supply duct |
| 220 | compressed gas supply reservoir | 222 | compressed air water and dirt filter |
| 224 | pressure/gas flow regulator | 226 | air compressor |
| 302 | shear fracture area | 304 | brittle fracture area |
| 306 | total fracture area | 310 | reference line for lateral expansion |
| 311 | lateral expansion line for $A_1$ | 312 | reference line for lateral expansion |
| 313 | lateral expansion line for $A_2$ | 314 | reference line for lateral expansion |
| 315 | lateral expansion line for $A_3$ | 316 | reference line for lateral expansion |
| 317 | lateral expansion line for $A_4$ | 404 | cover |
| 406 | strain gage circuit wires | 450 | excitation voltage |
| 452 | output voltage | 454 | active strain gage on left of striker |
| 456 | active strain gage on right of striker | 458 | balancing resistor |
| 459 | balancing resistor | 502 | calibrated load cell |
| 504 | rigid plate attached to tensile machine | 506 | rigid plate |
| 508 | rigid plate attached to tensile machine | 510 | center of strike |
| 602 | expandable member | 604 | hydraulic jack piston |
| 606 | calibrated load cell | 608 | top member of force reaction frame |
| 610 | right side member of force reaction frame | 612 | bottom member of force reaction frame |
| 614 | left side member of force reaction frame | | |

DETAILED DESCRIPTION OF THE INVENTION AND BEST MODE FOR CARRYING OUT THE PREFERRED EMBODIMENT

Prior Art

Figure 2:
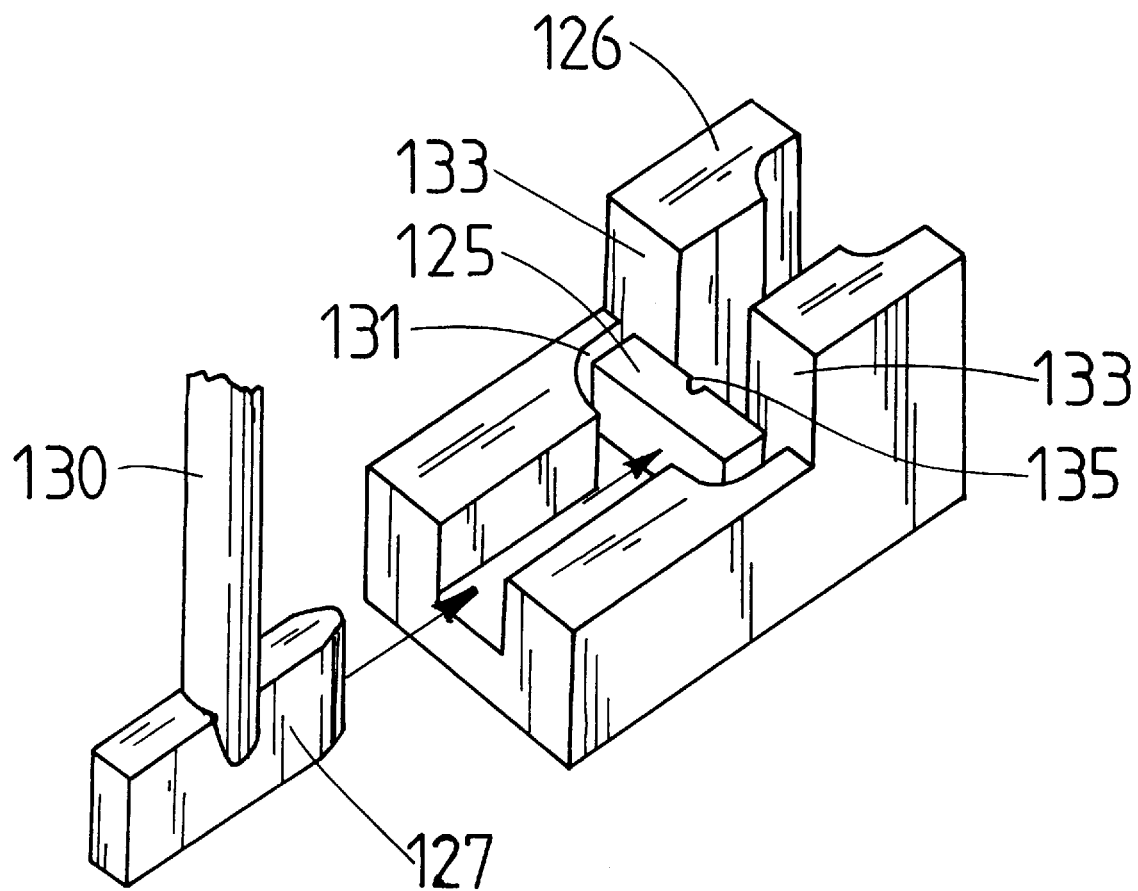
FIG. 2 is a schematic enlarged perspective view of the striker, anvils, and specimen support portion of the apparatus in FIG. 1.

Referring to FIGS. 1 and 2, prior art ASTM methods and apparatus are shown determining the energy absorbed by a solid material during a fracture test in which a specimen 125 is placed on specimen supports 128 against anvils 126 and dynamically impacted by a striker 127. The striker 127 is suspended on a pendulum arm 130 that rotates on a trunnion axis 129. The anvils 126 are provided with a specimen receptacle 131 to receive the specimen 125 which is positioned against anvil ledge faces 133.

Figure 3:
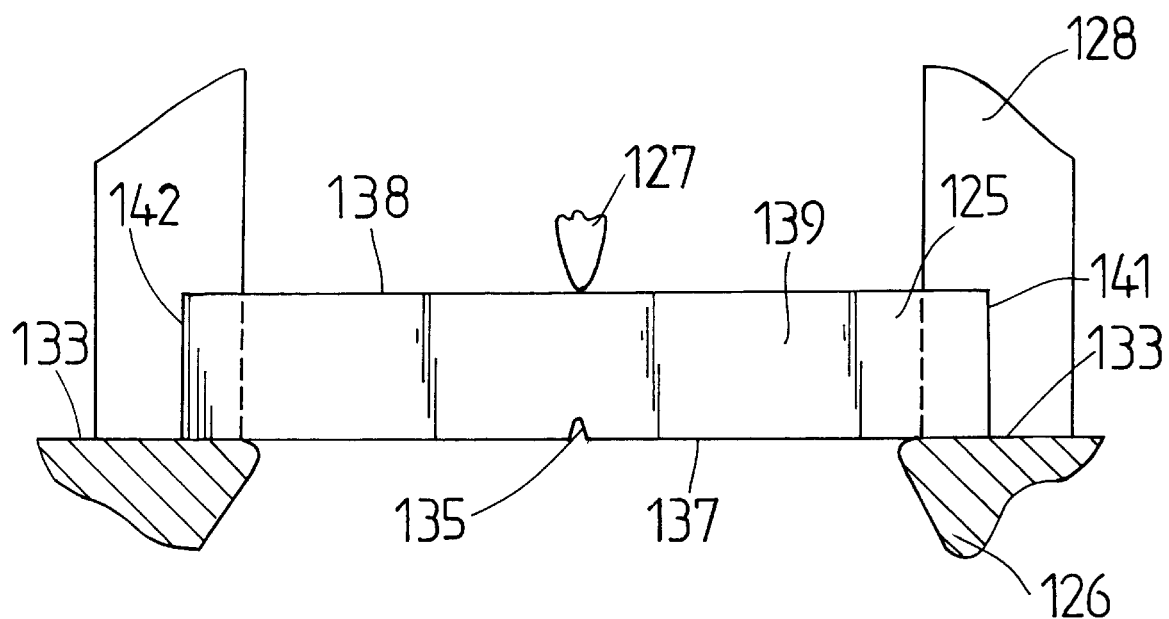
FIG. 3 is an elevational view of one of the fracture specimens (Charpy V-notch) specified for use in ASTM standard E 23, showing it position on the anvils.
Figure 4:
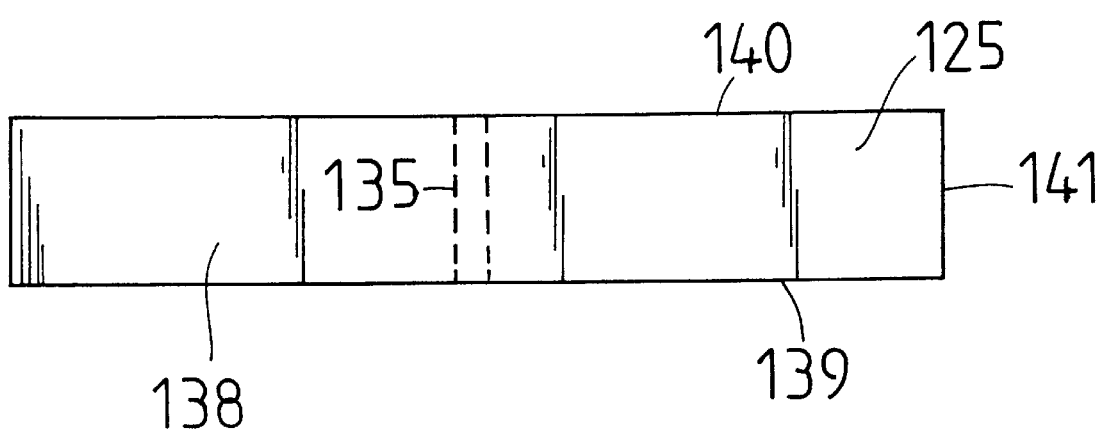
FIG. 4 is a plan view of the specimen shown in FIG. 3.

As most clearly seen in FIGS. 3 and 4, the specimen 125 is provided with a notch 135 on one elongated side 137. The specimen 125 shape is specified in ASTM standard E 23 and comprises two pairs of elongated parallel sides including a bottom side 137 which is notched, atop side 138 which is impacted by striker 127, and with sides normal to the notched side 139 and 140. The side 139 is normal to the notched side opposite side 140. The side 140 is normal to the notched side and rests on the specimen support. Square ends 141 and 142 are parallel to each other. Striker 127 is positioned intermediate anvils 126 and impacts specimen 125 on impact surface 138.

Figure 5:
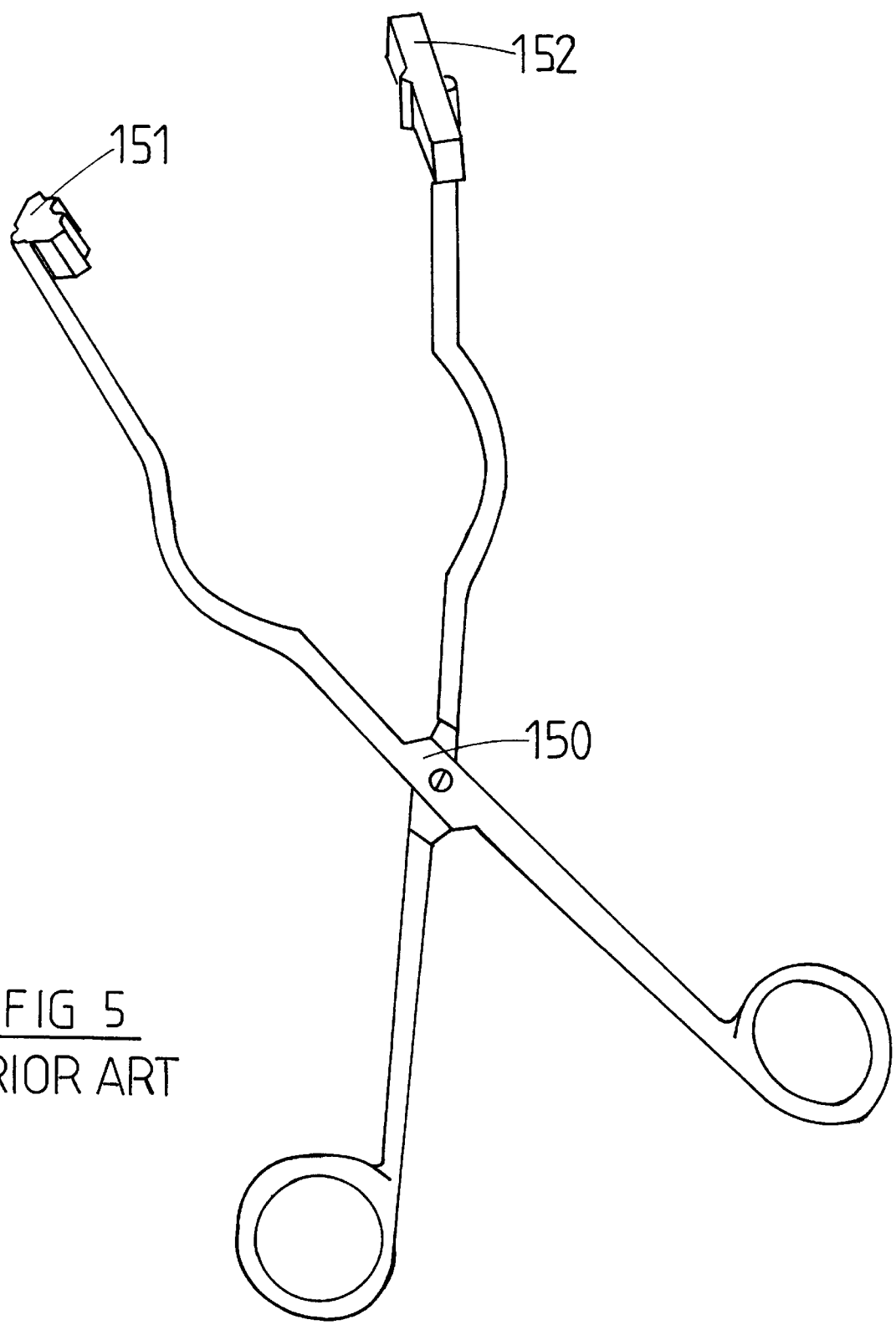
FIG. 5 is a schematic perspective view of the centering tongs used to center a conventional Charpy specimen on the specimen supports against the anvils as shown in FIGS. 2 and 3.

Referring to FIG. 5, centering tongs 150 are recommended in ASTM standard E 23 for transferring a Charpy specimen from a thermal conditioning medium to specimen supports 128. A specimen holding piece 151 holds the specimen against anvil surfaces 133 as a notch centering piece 152 passes between anvils 126.

Figure 6:
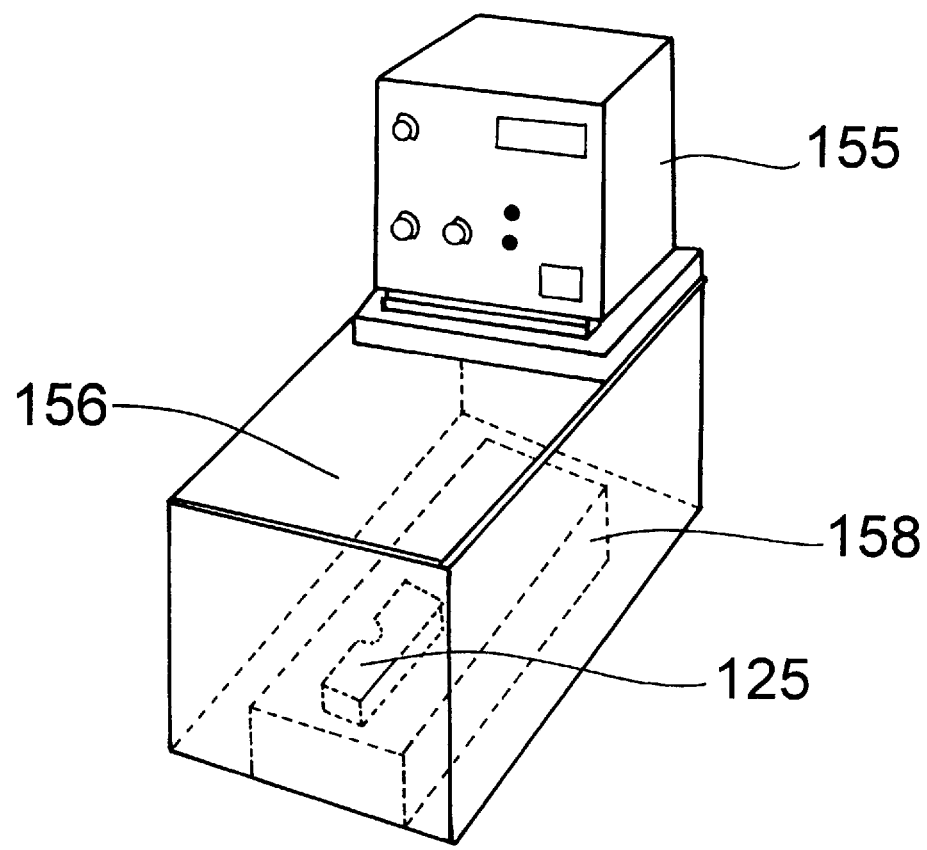
FIG. 6 is a schematic perspective view of an agitated bath which is used to thermally precondition a specimen to the desired test temperature just prior to transferring the specimen to the supports against the anvils using the centering tongs of FIG. 5.

Referring to FIG. 6, a typical thermal conditioning apparatus 155 with agitation and temperature control of a liquid bath 156 is used to thermally condition specimen 125 prior to transfer to the testing machine. ASTM standard E 23 requires specimen 125 to be placed on a raised grid 158 which supports specimen 125 at least 25 mm from the bottom of agitated liquid bath 156. ASTM E 23 requires that the mechanism used to remove the specimen from the thermal conditioning medium (centering tongs 150) be left in the medium except when handling the specimen so that the temperature disturbance to the specimen is minimized. ASTM standard E 23 recommends the use of centering tongs 150 as the preferred mechanism to transfer specimen 125 to the test machine.

Best Mode—In-Situ Thermal Conditioning

Figure 7:
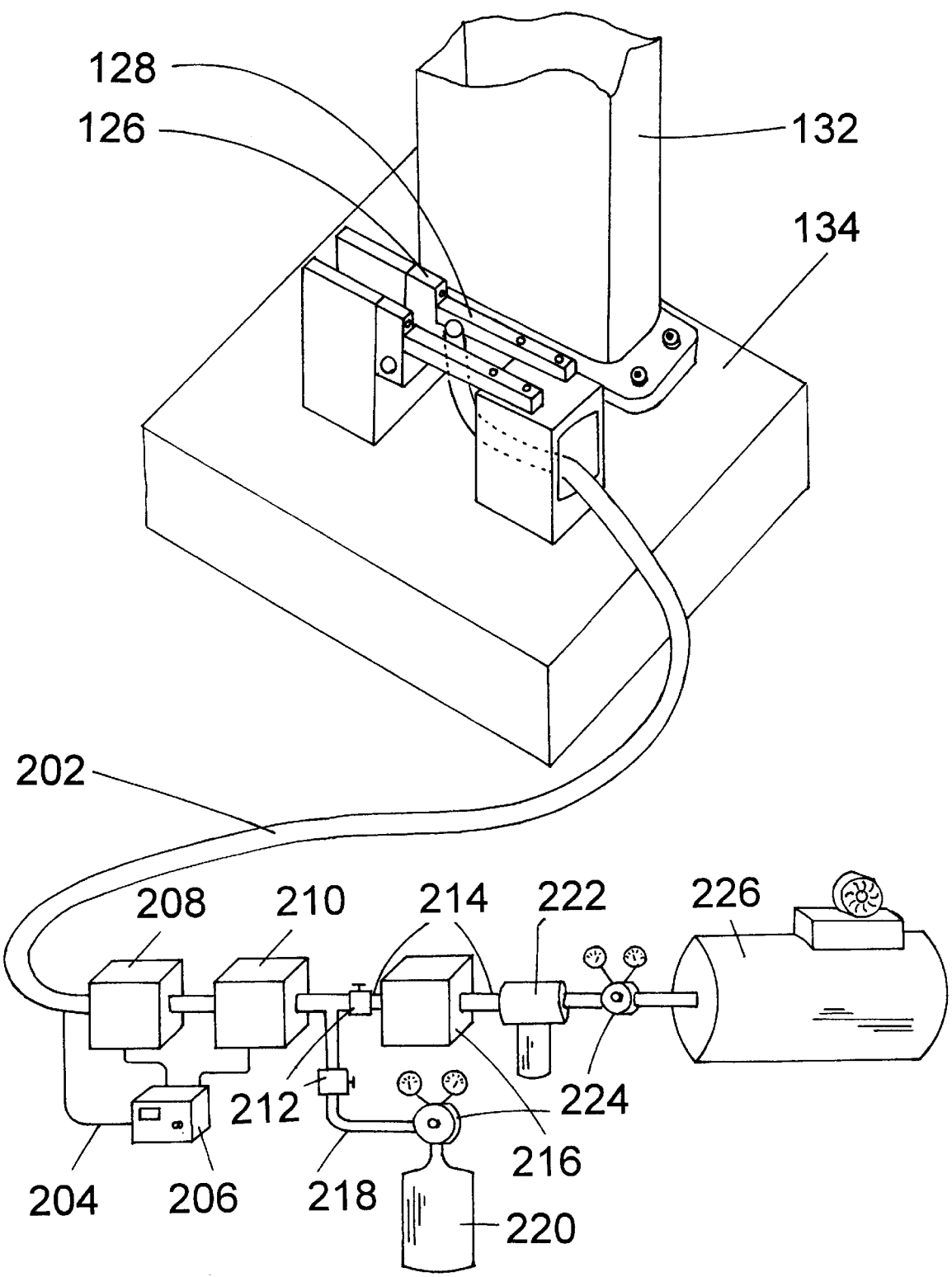
FIG. 7 is a schematic perspective view of the in-situ heating and/or cooling apparatus.

Referring to FIG. 7, a typical process according to this invention is carried out by supplying compressed air from an air compressor 226 and/or from a compressed gas supply reservoir 220. An air compressor is available from several suppliers such as Grainger, 4320 Lewis Road, Harrisburg, Pa. 17111 and a typical compressor is the Dayton Model 5F233A 10 HP pressure-lubricated two stage air compressor. The air compressor pressure and air flow rate may be controlled by a pressure/gas flow regulator 224. Similarly, the compressed gas supply reservoir 220 pressure and flow rate may be controlled by a pressure/gas flow regulator 224. A pressure/gas flow regulator may be obtained from any of several suppliers such as Grainger, 4320 Lewis Road, Harrisburg, Pa. 17111, and a typical pressure/gas flow regulator is the Harris Model 25-100-540, 0 to 100 psig regulator.

Referring to FIG. 7, gas from the compressed gas supply reservoir 220 flows in a gas reservoir supply duct 218 past a gas shutoff valve 212 to a gas refrigeration unit 210. Similarly, air from compressor 226 flows through a compressed air water and dirt filter 222 to remove dirt and moisture from the air. After passing through the filter 222, the air flows through compressed air supply duct 214 to air dryer unit 216 and then on to the gas refrigeration unit 210. If the desired specimen 125 test temperature is below room temperature, the refrigeration unit 210 may be used solely to achieve the desired specimen temperature. However, there are advantages associated with running the refrigeration unit in a continuous cooling mode and using a gas heating unit 208 to raise the temperature to the desired level. This approach has the advantage of reducing the wear and tear on the refrigeration unit 210 compressor and also provides a more stable temperature control because the temperature controller in the gas heating unit 208 has a known constant load with which to apply heat against. A gas temperature control thermocouple 204 is connected to a thermally conditioned gas delivery duct 202 and is used to measure the temperature of the gas which is delivered to specimen 125. The thermocouple 204 is connected to a gas temperature controller 206 which controls the gas heating unit 204 and/or the gas refrigeration unit 210. In the preferred mode, the refrigeration unit is run in a continuous cooling mode and, therefore, only the gas heating unit 208 need be controlled. The gas refrigeration unit 210, the gas heating unit 208, the controller 206, and the thermocouple 204 have been incorporated into a single commercially available unit by FTS Systems, Inc., PO Box 158, Rt 209, Stone Ridge, N.Y. 12484, and a particularly useful model for testing in the range of −80° C. to 230° C. is the Turbo-Jet TJ-80.

Figure 8:
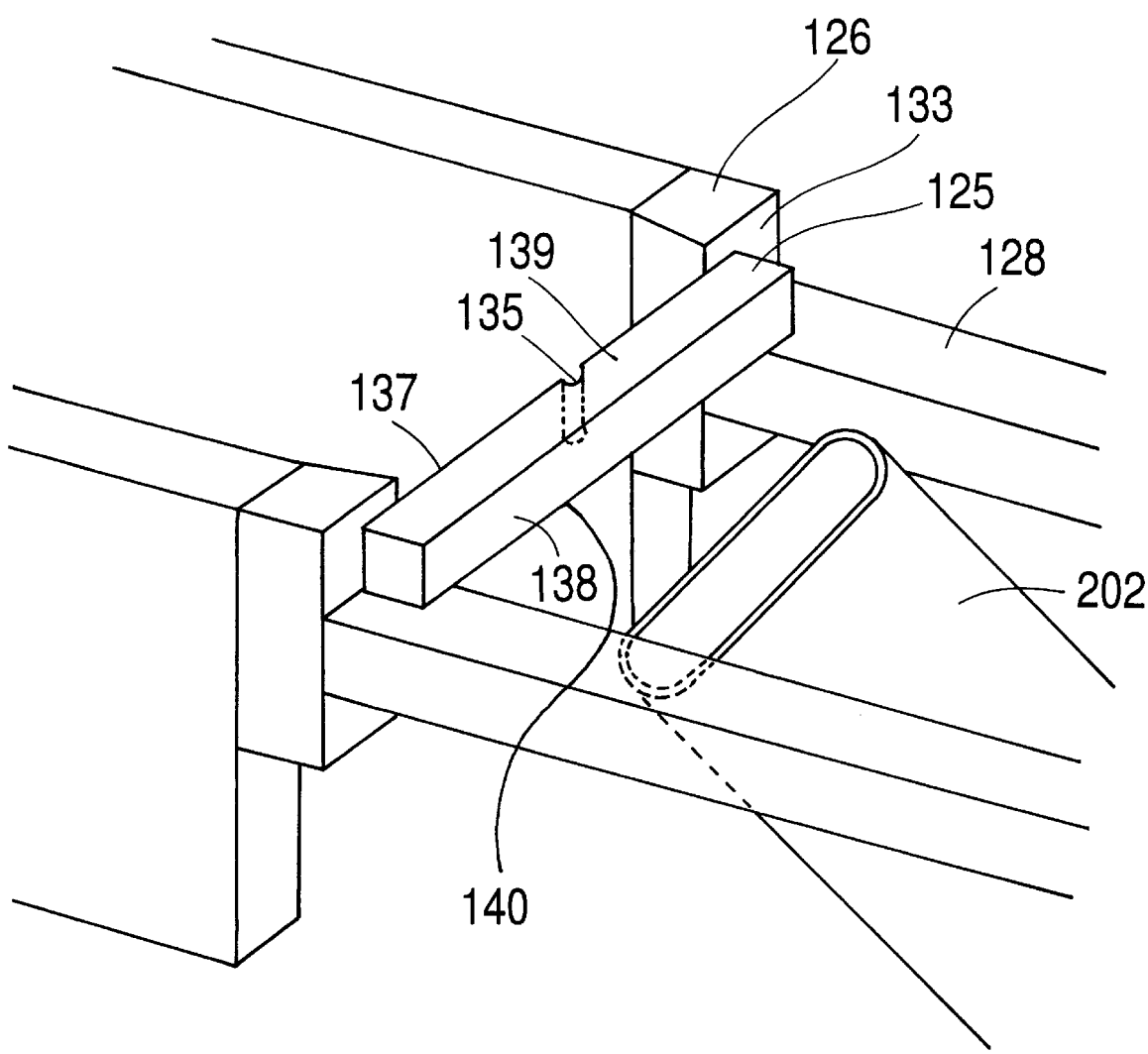
FIG. 8 is a schematic enlarged perspective view of the anvils, specimen support, specimen, and thermally conditioned gas delivery duct of the apparatus in FIG. 7.

Referring to FIGS. 7 and 8, the thermally conditioned gas delivery duct 202 is routed below the specimen supports 128 so that the pendulum arm 130 and striker 127 will not impact the gas delivery duct 202. Referring to FIG. 8, the end of the gas delivery duct 202 is positioned so that the gas flows around the surfaces of the specimen 125. In a preferred embodiment, the thermally conditioned gas is directed so that the flow splits at the intersection of specimen 125 surfaces 138 and 140 so that the specimen 125 is engulfed in the thermally conditioned gas. It is advantageous to direct at least part of the flow of the thermally conditioned gas onto surface 138 to ensure that specimen 125 remains in its aligned position on supports 128 against anvil ledge faces 133. It is also advantageous to control the gas flow rate because it is possible to levitate specimen 125 above specimen supports at high flow rates.

Figure 9:
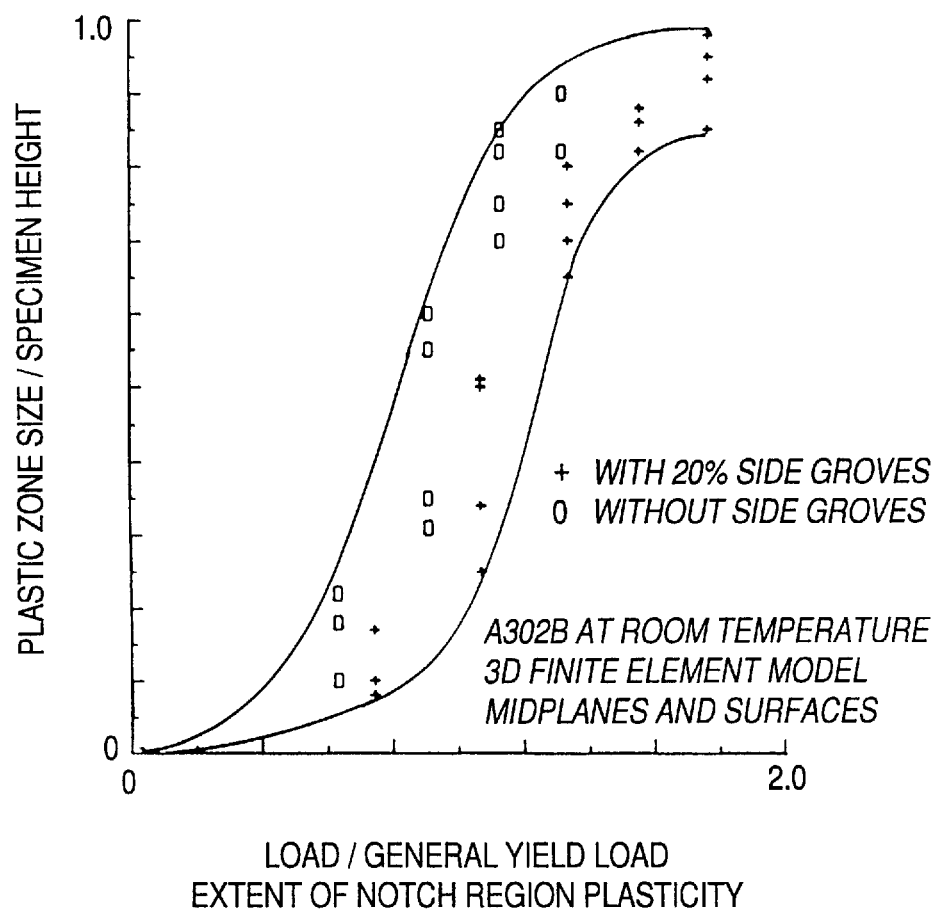
FIG. 9 illustrates plastic zone size results from three dimensional finite element simulations of Charpy V-notch specimens.

Referring to FIG. 9, three dimensional (3D) finite element simulations of Charpy impact specimens have shown that the plastic zone size in the vicinity of the notch or crack asymptotically approaches the size of the specimen height (H) at approximately general yield load. Therefore, the approximate volume of material which strongly influences the fracture properties is the uncracked ligament of width "H" (measured normal to the fracture plane) on either side of the crack plane. It is this approximate volume of material which must be accurately preconditioned thermally. Referring to FIG. 8, the portion of the specimen near the support will experience a thermal gradient as a result of heat flow between specimen 125 and supports 128 and anvils 126. However, since the Charpy specimen is approximately 5H long on either side of the crack plane as specified in ASTM standard E 23, the material at a position 1H, as measured from the crack plane of specimen 125 along the length of the specimen, is not significantly affected by heat flow to the anvils 126 or supports 128 because the central portion of the specimen containing the plastic zone is engulfed in the thermally preconditioned gas. This non-obvious discovery has been used for in-situ heating and cooling and it has been shown that very accurate results are obtained by thermally conditioning only the material in the vicinity of the notch and/or precrack. Optionally, supports 128 and anvils 126 may be thermally preconditioned to reduce heat flow near the ends of specimen 125, but support 128 and anvil 126 heating is not necessary to achieve accurate test results.

Figure 10:
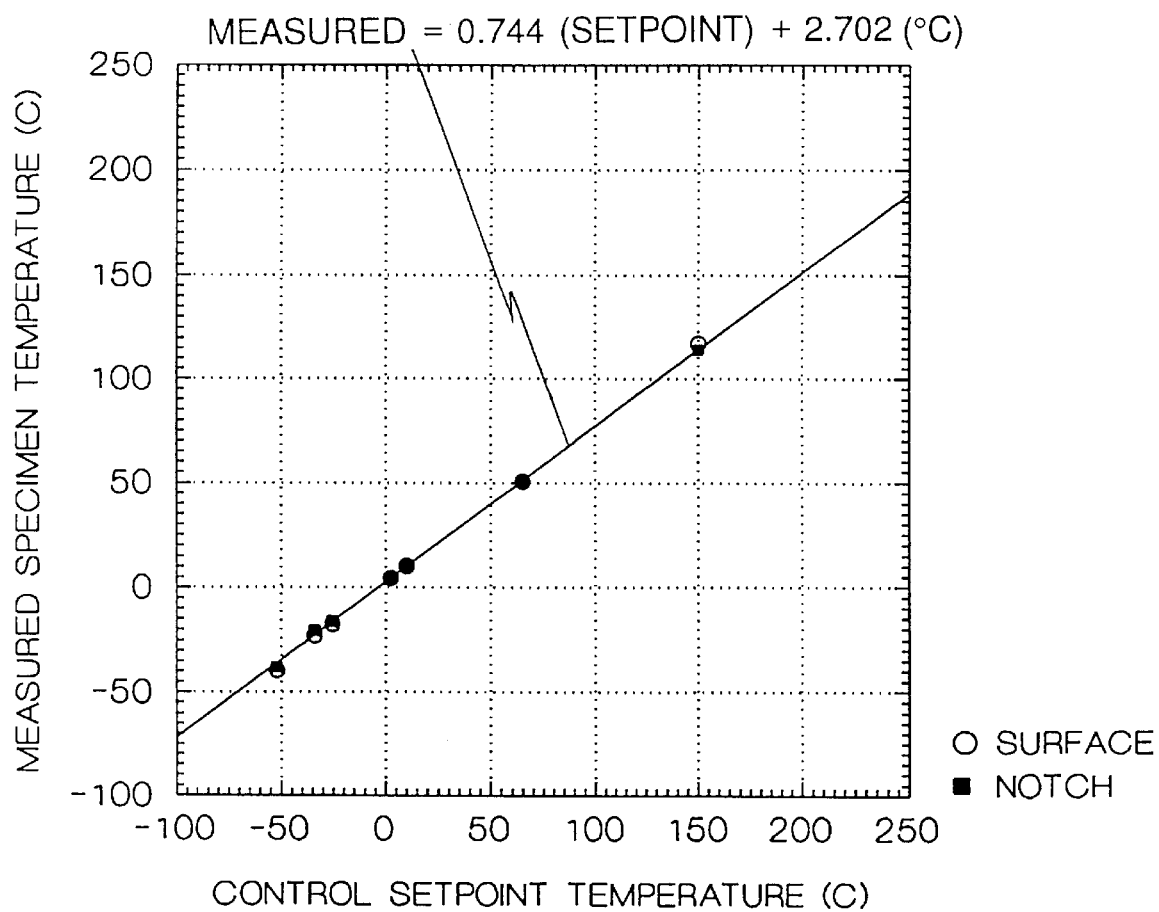
FIG. 10 illustrates Charpy specimen in-situ thermal conditioning system calibration data and line fit.

Referring to FIG. 10, thermocouples were attached to the surface and embedded inside a Charpy V-notch specimen near the notch and the specimen was notch centered on specimen supports 128 against anvils 126 and thermally conditioned using air. The data and regression line in FIG. 10 provide a relationship between gas temperature control thermocouple 204 and the temperature of in-situ specimen 125. Once the calibration is obtained, specimens may be thermally conditioned to the desired temperature by controlling to a temperature which yields the desired specimen 125 temperature. This approach eliminates the need to measure the specimen temperature for every test. Optionally, the specimen temperature may be measured for every test by attaching thermocouples or by using non-contact temperature measurement techniques such as infrared (IR) radiation emission measurement. A wide variety of IR temperature measurement instruments are commercially available from Raytek, Inc., 1201 Shaffer Road, Santa Cruz, Calif. 95061.

Figure 11:
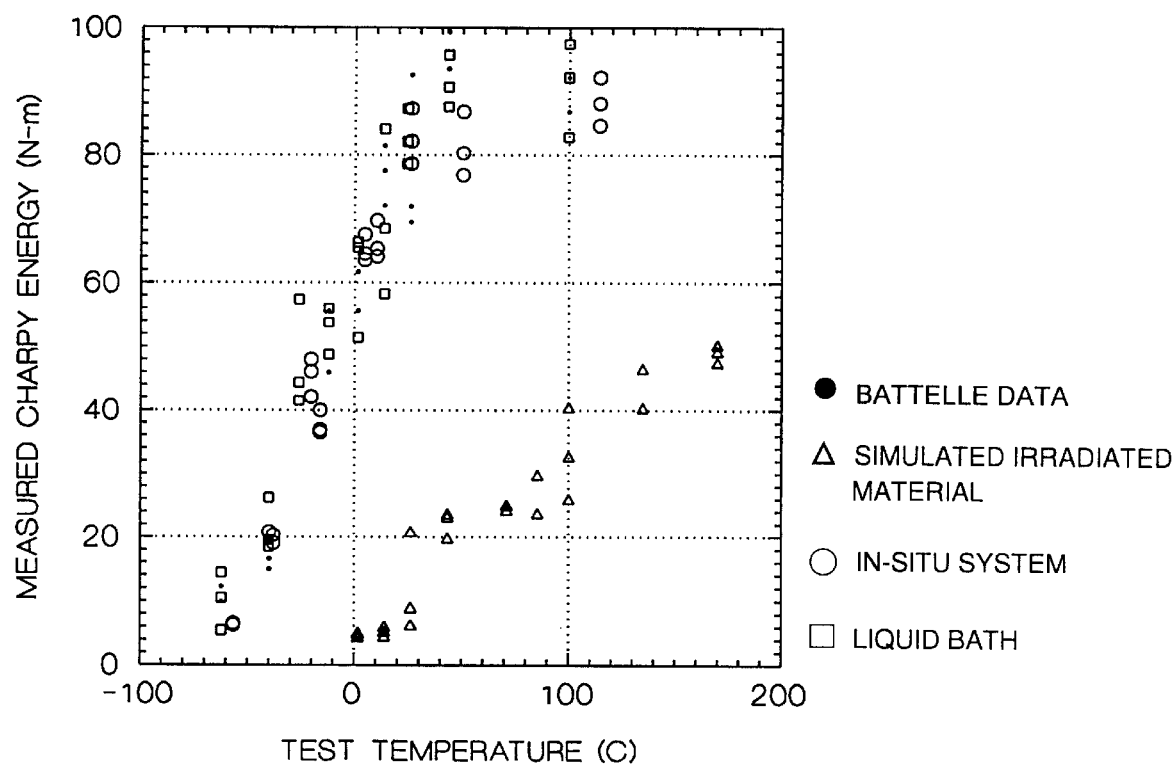
FIG. 11 illustrates the accurate data obtained testing Charpy V-notch specimens using in-situ air thermal conditioning system by comparing the in-situ data with data obtained using a conventional liquid bath (ASTM E 23 procedure) for specimen thermal conditioning.

Referring to FIG. 11, verification of the accuracy of data obtained from specimens which are thermally conditioned in-situ was obtained by comparison with data from specimens which were thermally conditioned using a liquid bath and transferred to the supports using centering tongs in accordance with ASTM E 23. The scatter bands for the in-situ tests were comparable to and slightly smaller than for the tests performed using the ASTM E 23 test procedure.

Best Mode—Upper Shelf Energy Determination in Miniature Specimens

Earlier attempts to calculate the USE of a CVN from MCVN data have failed because the stress fields in the MCVN specimens do not simulate the CVN fields and the fracture process volume (FPV) is not correctly calculated. The patented sidegrooving technique (references 1, 2, 3) was developed for stress field simulation of CVN stress fields in MCVN specimens. The sidegrooving technology provides the groundwork for the development of a procedure for accurately calculating the FPV, which in turn, enables accurate estimation of USE which would be obtained from testing CVN specimens using MCVN data. It was discovered that the FPV can be determined from:

$$FPV = bB\ (2H)$$

where,

FPV=fracture process volume
b=ligament length
B=specimen thickness
H=specimen height The data supporting this estimation is shown in FIG. 9. For a specimen with a square cross-section, this equation may be rewritten as:

$$FPV|_{square} = 2bB^2$$

Incorporating actual specimen dimensions of the CVN and MCVN specimens (reference 4) yields:

$$FPV|_{CVN} = 1,600.0\ mm^3$$

$$FPV|_{MCVN} = 143.8\ mm^3$$

which results in an FPV ratio of 11.1.

Using these equations, the USE is calculated from:

$$USE|_{CVN} = (PZCF)\ (USE|_{MCVN})\ \frac{FPV|_{CVN}}{FPV|_{MCVN}}$$

where,

PZCF=plastic zone correction factor

The reason why the PZCF is needed is because the stress fields in the MCVN do not exactly simulate the CVN specimen stress fields. The PZCF is used to make the necessary adjustment.

It was discovered that the pre-maximum load energy to total absorbed energy ratio is nearly constant and equal in CVN and MCVN specimens. This is a very significant discovery because it shows that the pre-crack propagation plastic zone size can be used to determine the PZCF. The pre-crack propagation finite element data given in FIG. 9 can be used to obtain the PZCF. However, this approach requires tests on a similar material for calibration. A more direct approach, which has been shown to be valid, is to use the pre-maximum characteristic load data. As an example, for the A302B material of reference 4, the ratio of the maximum load to the general yield load for the CVN and MCVN is as follows:

$$\underline{CVN} \qquad \underline{MCVN}$$
$$\frac{P_m}{P_{gy}} = 1.370 \qquad \frac{P_m}{P_{gy}} = 1.322$$

The PZCF can be estimated by taking the ratio of these values. These ratios are in close agreement, and their ratio (0.96) is the PZCF which can be used to correct for plastic zone size. This results in:

$$USE|_{CVN} = (11.1)(0.96)(USE|_{MCVN})$$

For the simulated irradiated A302B material of reference 4, the ratio of the maximum load to the general yield load for the CVN and MCVN is as follows:

$$\underline{CVN} \qquad \underline{MCVN}$$
$$\frac{P_m}{P_{gy}} = 1.762 \qquad \frac{P_m}{P_{gy}} = 1.333$$

The PZCF is obtained by taking the ratio of these values as described earlier. This results in:

$$USE|_{VVN} = (11.1)(0.75)(USE|_{MCVN})$$

This approach yields MCVN determined USE data which agree well with the CVN data as shown below:

|  | USE(J) for as-received material | USE(J) for simulated irradiated material | USE(J) drop |
| --- | --- | --- | --- |
| USE measured using CVN | 91.2 | 48.8 | 42.4 |
| USE determined using MCVN and above describe calculation | 91.9 | 51.9 | 40.0 |

Best Mode—Percent Shear and Lateral Expansion Measurement

A computerized image capture system is used to provide an accurate digitized reproduction of the fracture surface of the fracture specimen at low magnification. This invention applies to both conventional ASTM E 23 specimens and to miniaturized specimens. A camera with a low magnification lens provides a signal to a frame grabber card in the data acquisition computer. The signal is routed from the computer to a video monitor. It is necessary to adjust the lighting so that the faceted brittle fracture region appears as a bright and shiny area in contrast to the dull and fibrous ductile fracture region of the fracture surface. Once the desired image is focused and displayed on the video monitor, the image is digitized and saved to disk. The digitized image is then calibrated and precise area and length measurements can be made on the computer image. It is preferable to include a calibrated reticle in the captured image so that the length and area measurements can be calibrated. If the calibration is done using a calibrated reticle is a separate captured image, it is important to capture the image before the magnification is changed. An image analysis program is then used to measure the percent shear fracture area and the lateral expansion. Such a program can be written for this purpose or one of several commercially available programs, such as SigmaScan/Image by Jandel, PO Box 7005, San Rafael, Calif., may be used.

Figure 12:
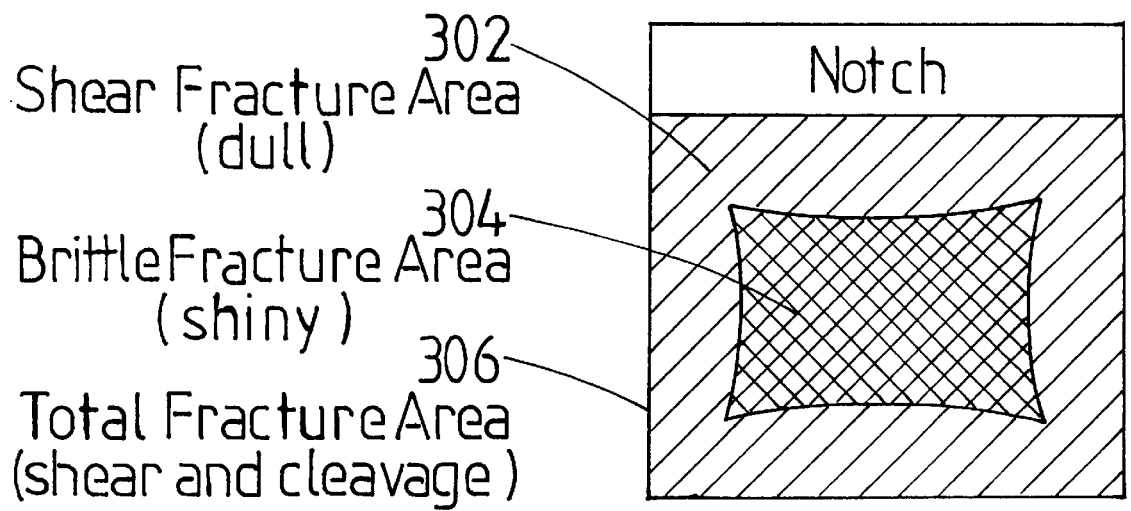
FIG. 12 illustrates the fracture surface of a Charpy specimen after an impact test at a temperature which yields both brittle and ductile areas within the fracture surface.

If necessary, the image may be enhanced by brightening the pixels which contain the bright faceted region. Experience has shown that the image can be enhanced adequately prior to capture using appropriate lighting. Referring to FIG. 12, a cursor is used to outline the brittle fracture area 304 ($A_b$) and the total fracture area 306 ($A_t$). Total fracture area 306 includes shear fracture area 302 and brittle fracture area 304, but does not include the area of the specimen associated with the machined notch. The outlined areas are then calculated by the computer program and the percent shear fracture area is computed as follows:

percent shear fracture area=100 $(1-(A_b/A_t))$

Figure 13:
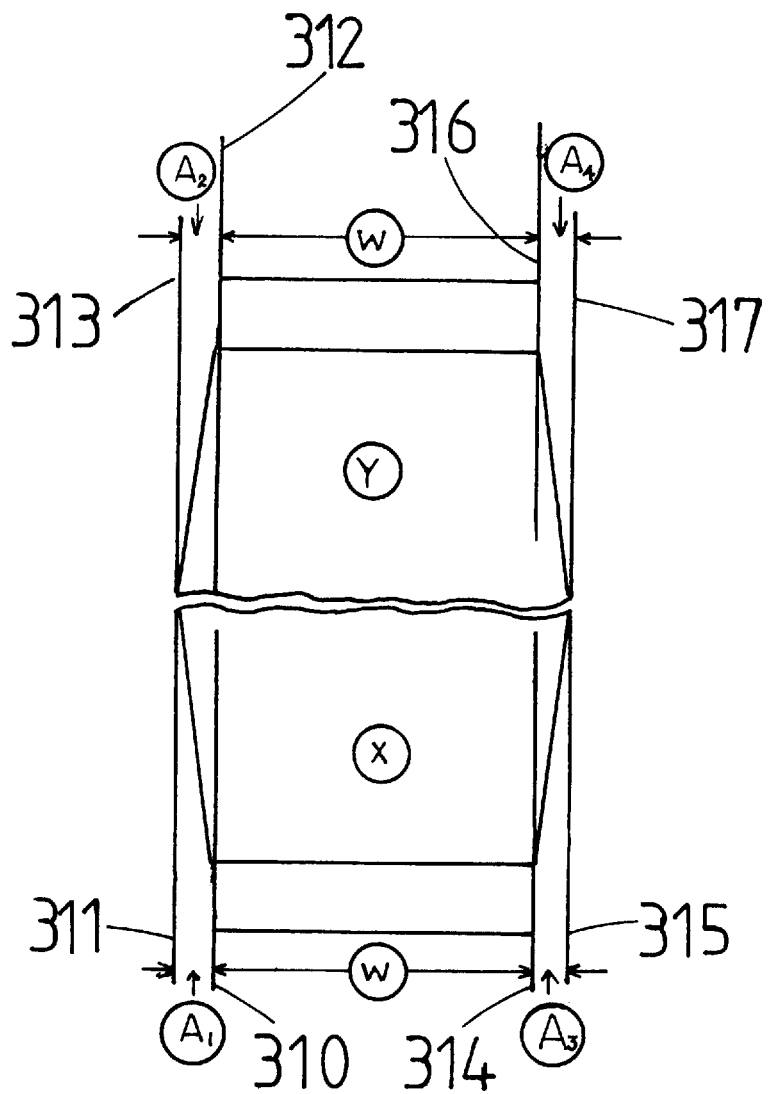
FIG. 13 illustrates the broken halves of a Charpy specimen (half X and half Y) as defined in ASTM E 23 showing the measurement of lateral expansion dimensions $A_1$, $A_2$, $A_3$, $A_4$, and original width (W).

Lateral expansion is measured in accordance with the requirements of ASTM E 23 using the captured image of the fracture surface. Referring to FIG. 13, a lateral expansion reference line 310 is drawn along the fracture surface in the direction of crack propagation which is parallel to, and coincident with, the side of the machined notch. A lateral expansion line 311 is drawn parallel to reference line 310 which intersects the material point which extends farthest outward from the notch side. The lateral expansion dimension $A_1$ is measured using the computer program by measuring the shortest distance between lines 310 and 311. This procedure is repeated using reference line 312 and lateral expansion line 313 to obtain lateral expansion dimension $A_2$, using reference line 314 and lateral expansion line 315 to obtain lateral expansion dimension $A_3$, and using reference line 316 and lateral expansion line 317 to obtain lateral expansion dimension $A_4$. In accordance with ASTM E 23, the lateral expansion is the sum of the greater of ($A_1$ or $A_2$) and the greater of ($A_3$ or $A_4$).

The lateral expansion measurement invention can be used for conventional impact specimens and for miniaturized impact specimens. In cases where sidegrooved specimens are used, as described in references (2) and (3), conventional lateral expansion gages as described in ASTM E 23 cannot be used because the reference surface of the lateral expansion gage does not fit into the groove. The invention is a non-obvious solution to this problem.

The invention provides a means for accurately and cost effectively measuring the percent shear fracture area and lateral expansion of conventional and miniature impact specimens. Referring to FIGS. 14, 15, 16, and 17, the importance of making these measurements is illustrated and further inventions and preferred embodiments are described. It is first observed that lateral expansion, percent shear, and absorbed energy exhibit mixed mode, or transitional fracture behavior, over substantially the same temperature range. However, on comparing FIGS. 14 and 15, it is observed that the heat treatment causes an upward temperature shift of the energy-temperature curve, a drop in the upper shelf energy, and a decrease in the transition region slope. Within the nuclear industry, allowable pressure-temperature (P-T) operating curves are calculated based on the shift due to irradiation indexed at the 41 J level, and neither percent shear nor lateral expansion are used in P-T curve calculations. The use of percent shear is shown to be a more accurate and appropriate measure of the shift in the transition region in FIGS. 14 through 17 because there is not a large change in the slope of the percent shear-temperature curves. The choice of the index for percent shear does not have a significant impact on the curve shift results and an index of 50% shear is a reasonable index. The use of percent shear is a more logical choice for tracking radiation embrittlement because it is a more fundamental definition of transitional fracture than total absorbed energy or lateral expansion. Further, because of the slope change of the energy-temperature curve with embrittlement, the amount of percent shear is continuously increasing with embrittlement when 41 J of absorbed energy is used as the Charpy shift index.

Figure 14:
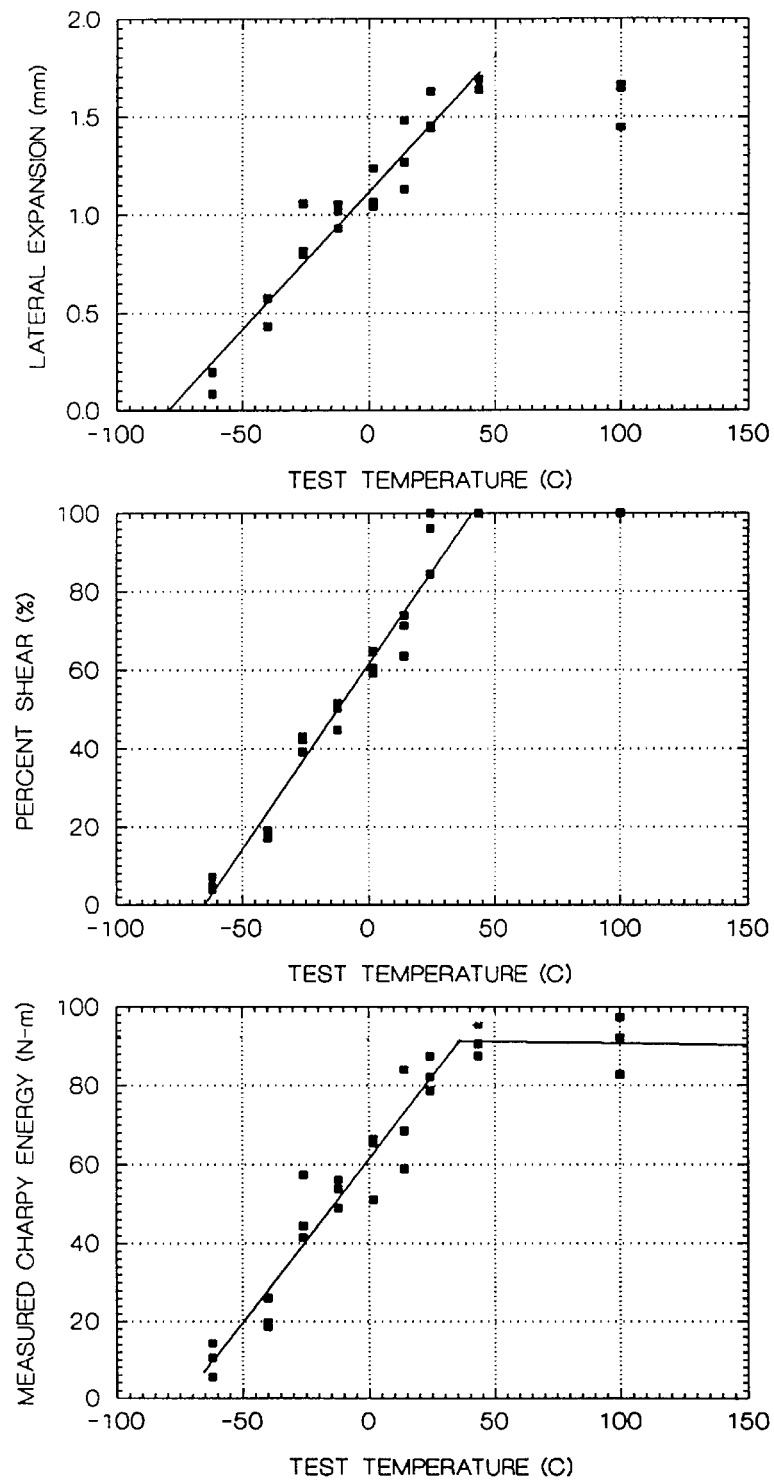
FIG. 14 illustrates Charpy data (conventional specimens) for as-received A302B reactor pressure vessel steel tested using the invention methods and apparatus including: instrumented striker; in-situ thermal conditioning; and fracture surface imaging and analysis system.
Figure 15:
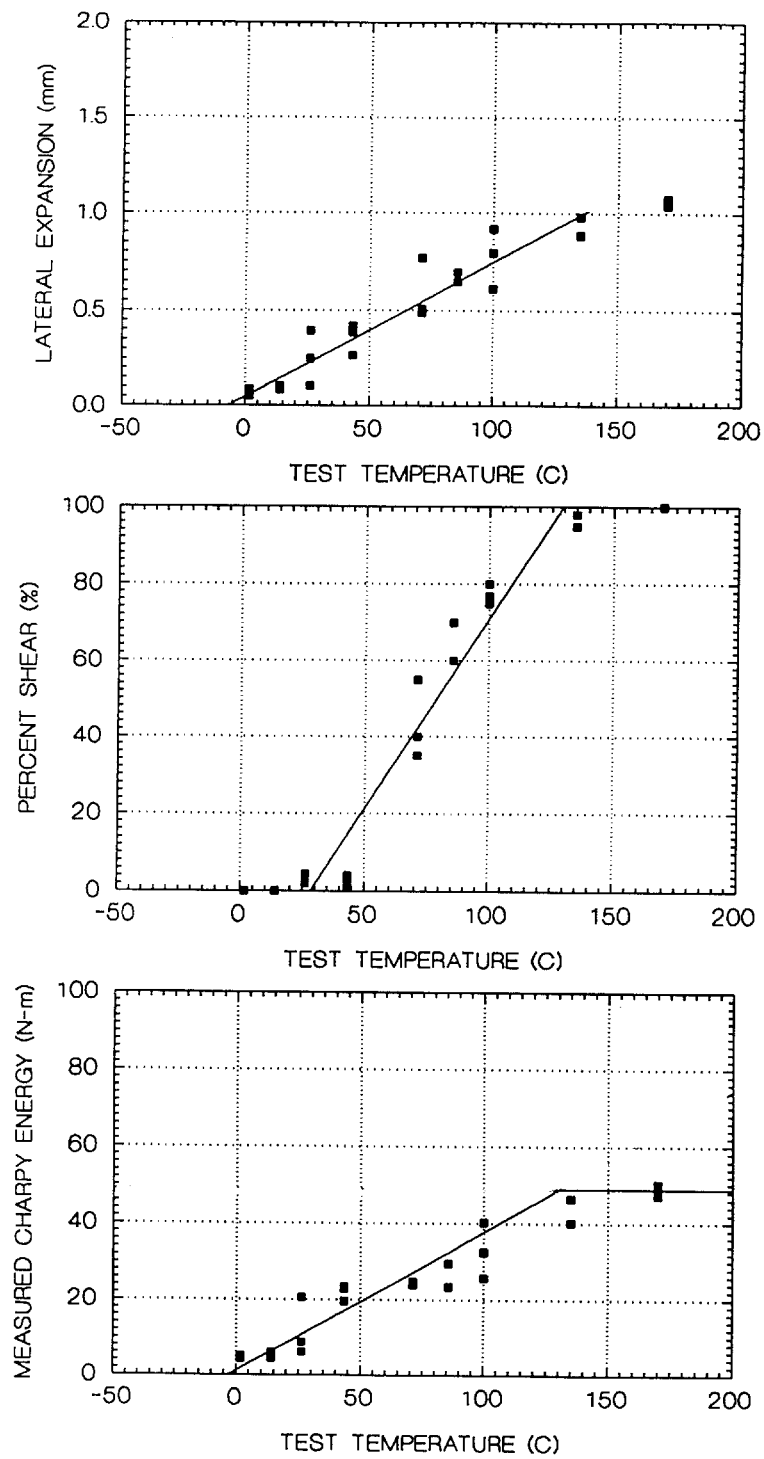
FIG. 15 illustrates Charpy data (conventional specimens) for simulated irradiated A302B reactor pressure vessel steel tested using the invention methods and apparatus including: instrumented striker; in-situ thermal conditioning; and fracture surface imaging and analysis system.
Figure 16:
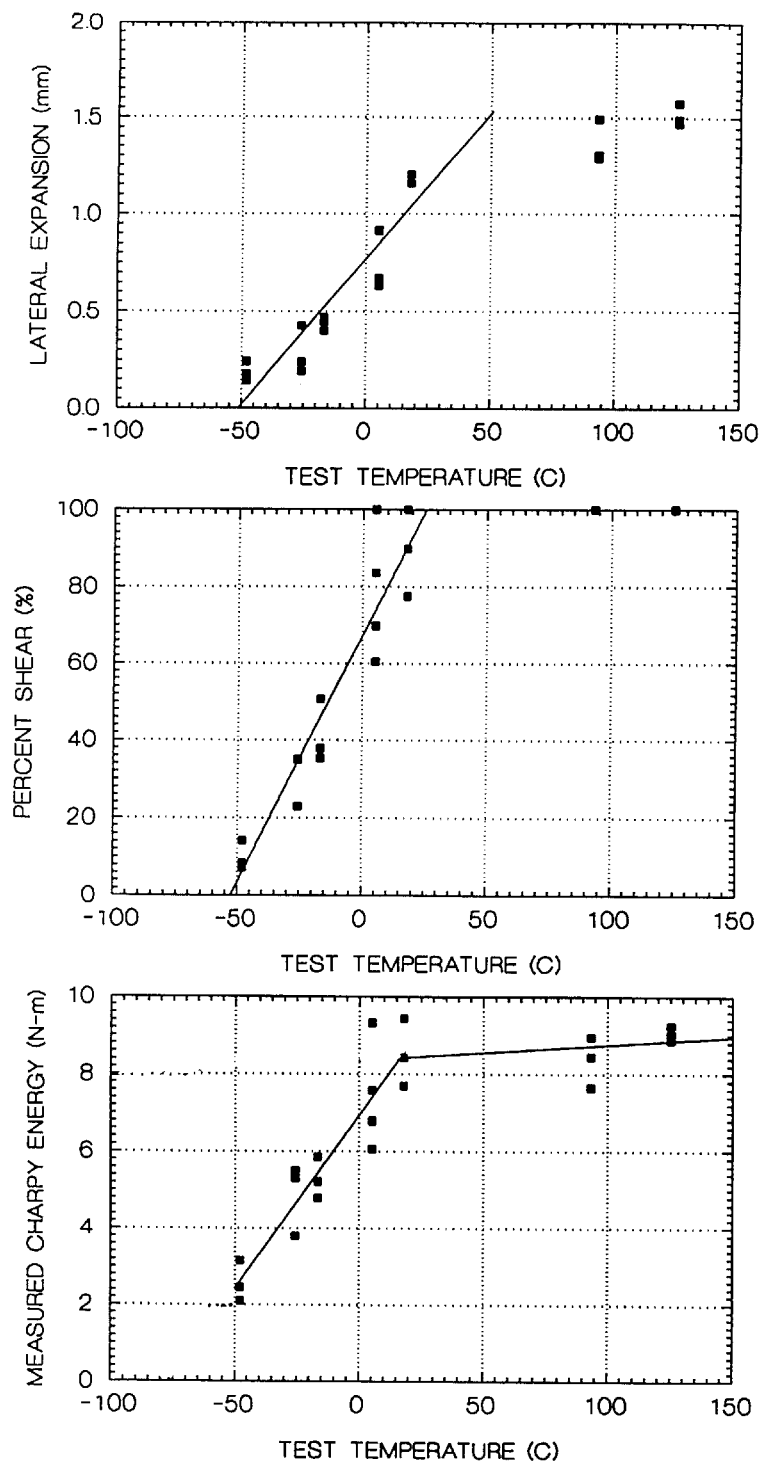
FIG. 16 illustrates miniature sidegrooved Charpy data for as-received A302B reactor pressure vessel steel tested using the invention methods and apparatus including: instrumented striker; in-situ thermal conditioning; and fracture surface imaging and analysis system.
Figure 17:
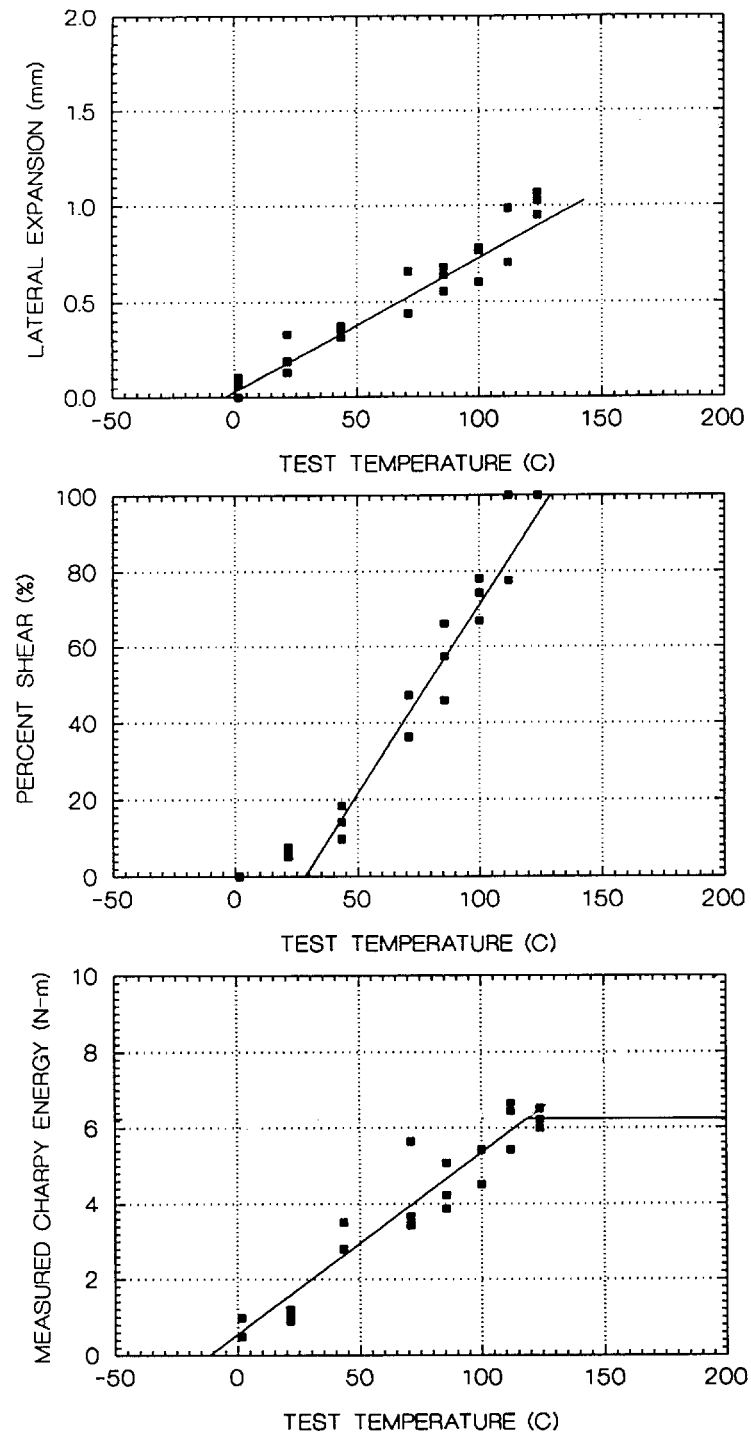
FIG. 17 illustrates miniature sidegrooved Charpy data for simulated irradiated A302B reactor pressure vessel steel tested using the invention methods and apparatus including: instrumented striker; in-situ thermal conditioning; and fracture surface imaging and analysis system.

The use of sidegrooves to increase the volume of material which is tested under plane strain conditions has been shown to yield negligible loss of constraint in the miniature specimens (compare FIGS. 14 and 15 with 15 and 16). Another advantage of using sidegrooved specimens is the fact that the magnitude of the measured lateral expansion from the miniature sidegrooved specimen is substantially the same as for the conventional specimen. This can be seen by comparing FIGS. 14 and 16 and FIGS. 15 and 17. This latter discovery is non-obvious and is important because no miniature specimen correction factors are needed to produce lateral expansion data using miniature specimens which is of substantially equal magnitude to data from conventional Charpy specimens. Similarly, the percent shear data are substantially equal in magnitude and temperature dependence for the MCVN and CVN data (compare FIGS. 14 and 16 and FIGS. 15 and 17). The fact that the lateral expansion and % shear data from miniature specimens is substantially equal quantitatively and exhibits substantially the same temperature dependence has never been observed before because, prior to the invention, it was not possible to obtain lateral expansion and percent shear data from miniature sidegrooved specimens.

Best Mode—Force-Time Measurement

Figure 18:
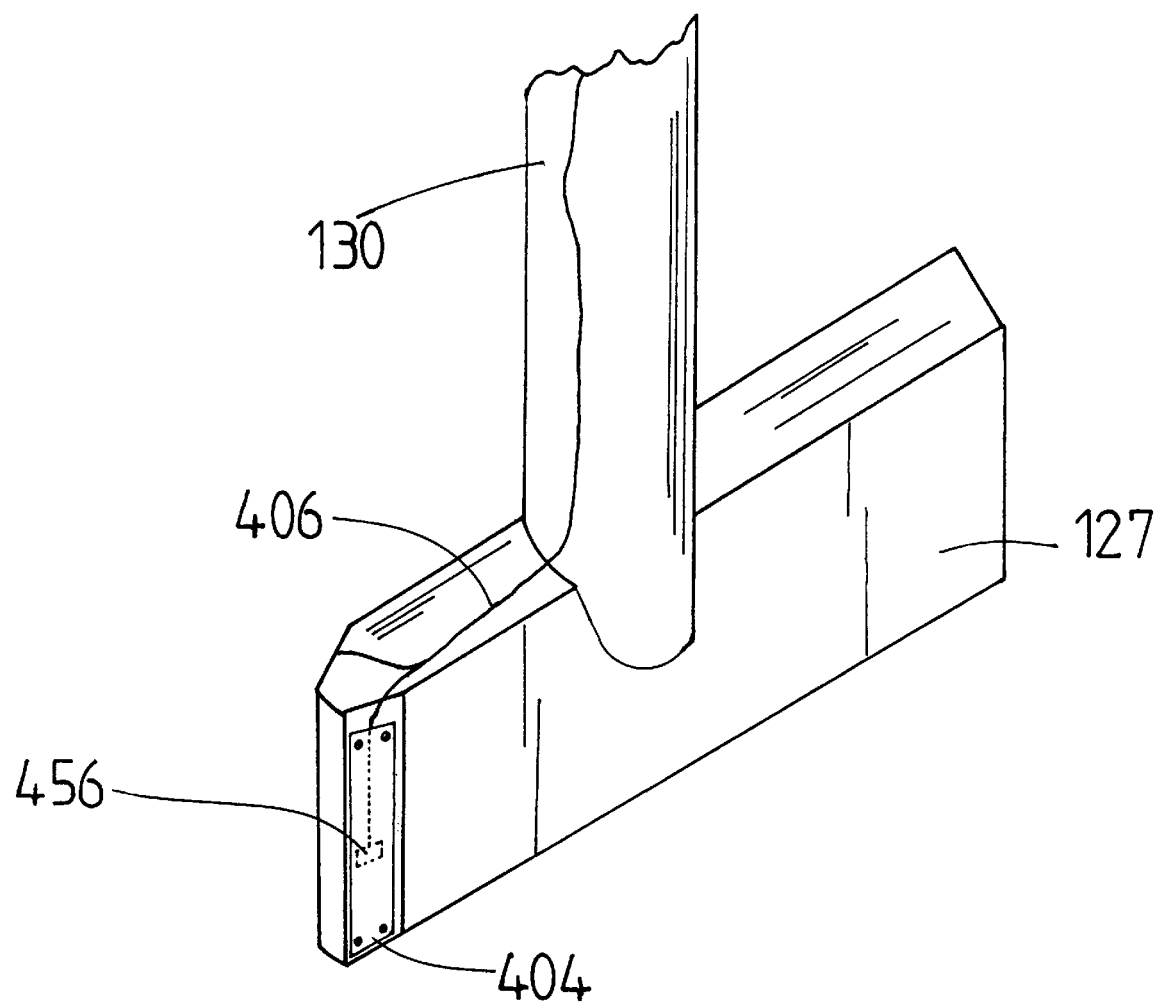
FIG. 18 is a schematic perspective view of an instrumented striker with strain gages attached for measurement of force-time data and showing covers attached to protect strain gages from impact by the fractured specimen halves and with strain gages mounted well within one stress wavelength of the impact surface.
Figure 19:
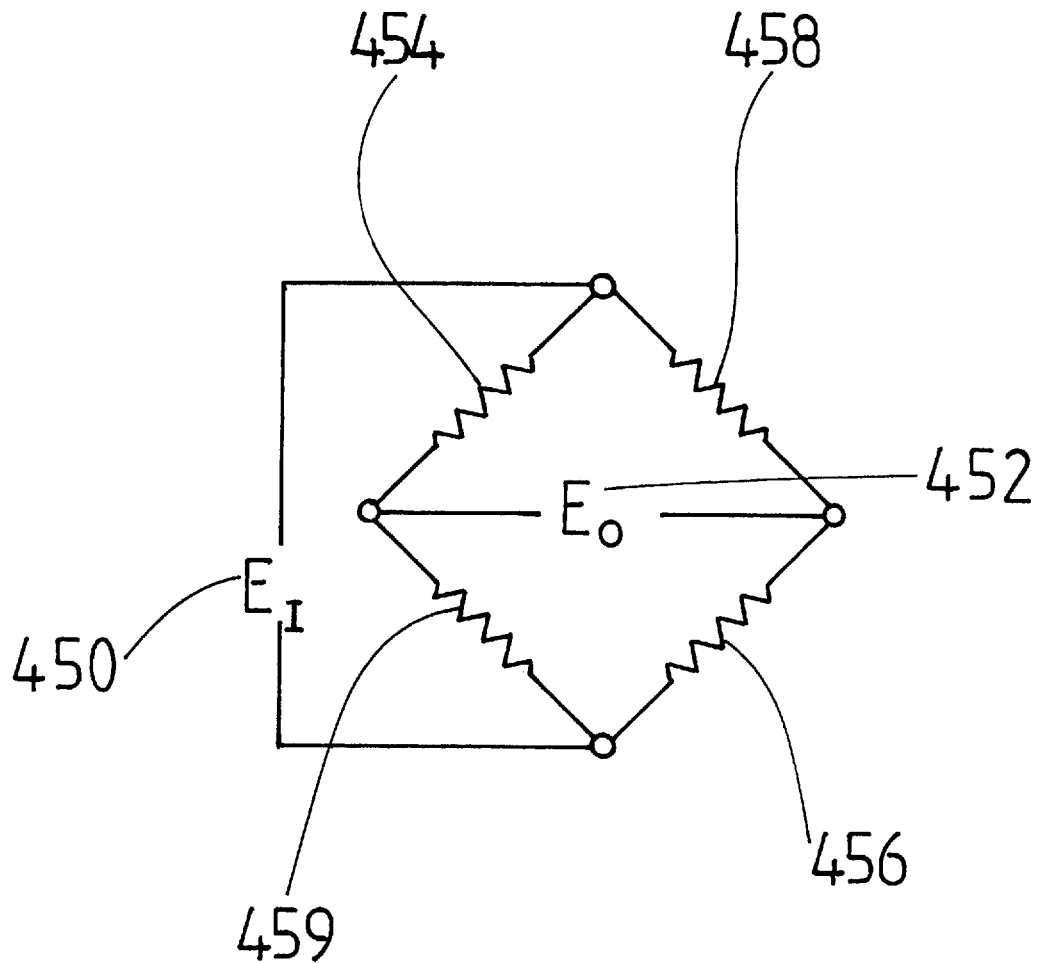
FIG. 19 illustrates the instrumented striker Wheatstone bridge which includes two active strain gages which are attached to the striker and two balancing resistors which are not attached to the striker or pendulum.

The preferred embodiment involves the application of two active strain gages on the "nose" of the striker as close to the impact interface between the striker and the specimen as is reasonable. In practice, two active gages are installed along the center of percussion on the tapered portion of the nose of the striker. For a pendulum with a distributed mass, the center of percussion is the radial distance (from the axis of rotation) at which and impact at the center of percussion will result in minimal reaction forces at the axis of rotation. Referring to FIGS. 18 and 19, an active strain gage 456 on the right side of striker 127 (viewed form the specimen side of the impact interface) and an active strain gage 454 on the left side of striker 127 are attached to tapered portion of striker 127 and are protected from specimen 125 impact by covers 404 which are screwed or otherwise held in place. Strain gage circuit wires 406 connect active strain gages 454 and 456 on the striker nose to balancing resistors 458 and 459 to form a Wheatstone bridge, and the Wheatstone bridge is connected, in a customary manner, to an amplifier and excitation voltage supply. Referring to FIG. 19, a Wheatstone circuit is shown which includes active strain gages 454 and 456 which are connected on opposite arms of the bridge to cancel or substantially reduce bending strain measurement. Balancing resistors 458 and 459 are included to complete the Wheatstone bridge. A unique feature of the invention is the use of two active gages on the striker and two balancing resistors which are not attached to the striker. Conventional load cell designs strive for temperature compensation by attaching all four resistors of the basic Wheatstone bridge to the spring element. In the invention, the balancing resistors are not attached to the striker to eliminate reflected stress wave effects and to provide the opportunity for locating the active gages as close to the impact location along the center of percussion as is practical. Since the impact event duration is on the order of 5 milliseconds, temperature compensation is not important. Experience with the invention shows that temperature changes which result in thermally induced strain signal changes occur on a time scale of minutes to hours. Although these effects are not significant, they can be substantially reduced by allowing the system to operate for ½ hour before data acquisition and by holding the laboratory temperature as constant as possible.

Another unique and non-obvious feature of the invention is the placement position of the active strain gages on the striker. Impact test equipment manufacturers design their test machines so that the center line of the specimen coincides with the center of percussion to ensure that the specimen is struck with minimal reaction forces at the axis of rotation. Since stress waves propagate from the impact contact location, it is desirable to attach the strain gages on the striker so that they are substantially coincident with the center line of the specimen, which, for a pendulum machine, is the center of percussion. However, further considerations described below show significant advantages if the gages are also moved as close as practical to the impact surface.

The force-time curve from an instrumented test can be integrated to yield the total absorbed energy. The absorbed energy from the test machine dial or optical encoder is used in the current art to obtain a calibration factor to "adjust" the integrated energy from the instrumented striker to match the machine energy. The correction factors are usually very large and an adequate explanation for the large magnitude of the correction factors has not been offered in the literature. Since the correction factors are large, the forces are not representative of the actual forces. This invention explains why the forces measured in the current art are not accurate. Instrumented tests which yield accurate characteristic load, deflection, velocity, and energy data are needed for correlations which yield material properties such as fracture toughness.

An impact force-time curve can be considered to be a linear superposition of many sinusoidal inputs of different frequencies (it can be represented as a Fourier series). The lowest frequency components of the force-time curve can be accurately measured with strain gages mounted almost anywhere on the striker. However, higher frequency components arise from ringing of the specimen during the initial elastic deformation stage of the test and from the initiation and arrest of unstable crack growth (brittle fracture event). Shortly after initial contact with the specimen, relatively large inertial forces accelerate the specimen to the speed of the striker. Since these inertial forces are large compared to the quasi-static load-deflection behavior of the specimen, the specimen begins to vibrate and can even loose contact with the striker during the elastic phase of the specimen deformation behavior. Therefore, the force exerted on the specimen by the striker has a component with a frequency that is equal to the lowest natural frequency of the specimen. For a standard Charpy specimen, finite element simulations have shown that this frequency is about 50 kHz. For a half scale miniaturized specimen, this frequency would be twice this value or 100 kHz.

The onset of unstable crack growth is another reason for the load record having higher frequency components. During unstable crack growth, the load that the specimen can support decreases very quickly due to the rapid increase in crack length. If a crack propagation speed of 60,000 in/sec is assumed, and it is assumed that the crack propagates across the entire ligament (0.315 in), then the load drop would occur in 5.25 microseconds. Doubling this time (to get a full cycle time) and inverting gives a frequency of about 100 kHz. For a half scale miniaturized specimen, the crack would propagate only half as far and therefore the frequency would be doubled to about 200 kHz.

Figure 20:
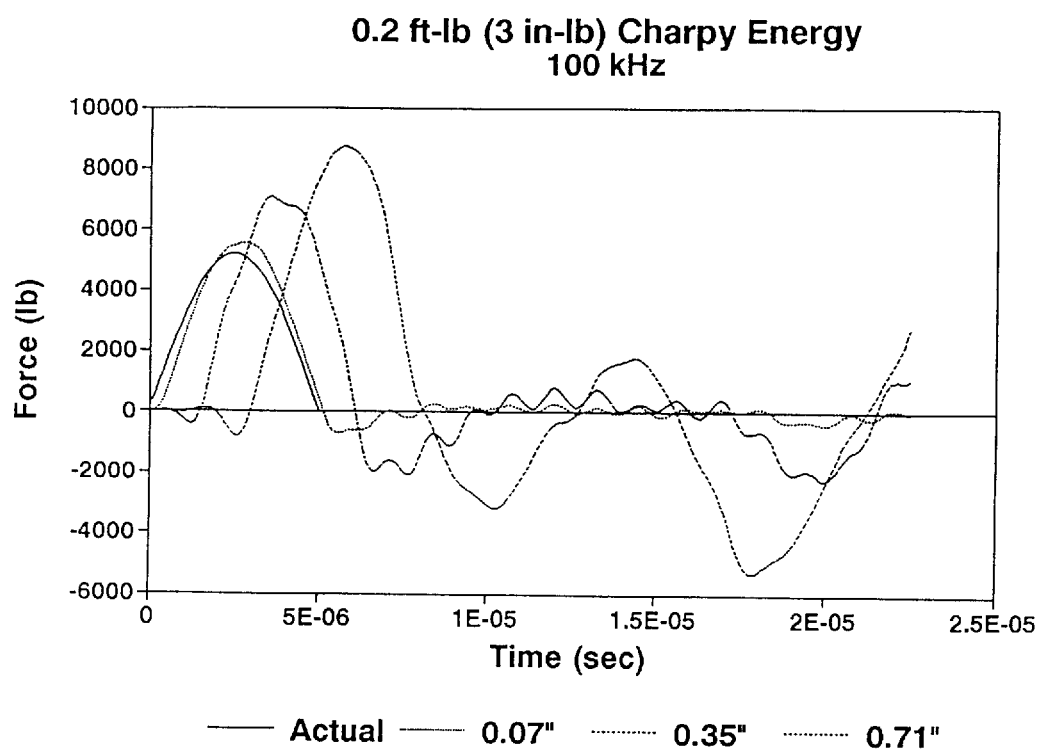
FIG. 20 illustrates the striker load cell response from a 100 kHz impulse load as a function of position of the strain gages on the surface of the striker measured from the impact location along the center of percussion.

Referring to FIG. 20, the results of finite element calculations with strain gages located at 0.07 inches, 0.35 inches, and 0.71 inches back from the impact location on the striker along the surface at the center of percussion are shown. When the gages are attached 0.07 inches or less behind the impact surface, a good simulation of the actual load response is obtained. However, it can be seen that the gages that are farther from the impacted surface tend to provide a larger peak load than was actually applied. Since this peak occurs before the reflected wave front interacts, it seems that this discrepancy is due to the stress-strain state between the impacted surface and the gage being different from the quasi-static state that would exist during static calibration. The closest load cell to the impacted surface (0.07 inch case) is seen to be much more accurate than the other two load cells (0.35 inch and 0.71 inch cases). It is believed that there are two principal reasons for this. First, by being closer to the contact surface, the dynamic stress-strain state tends to be more similar to the quasi-static state that exists during calibration. Second, by being closer to the surface, there is less mass between the gage and the surface that can lead to nonzero indications of load (due to inertial effects) when the actual load is zero. Overall, when the load cell strain gages are well within one stress wavelength of the striking surface, satisfactory load cell response can be expected.

Figure 21:
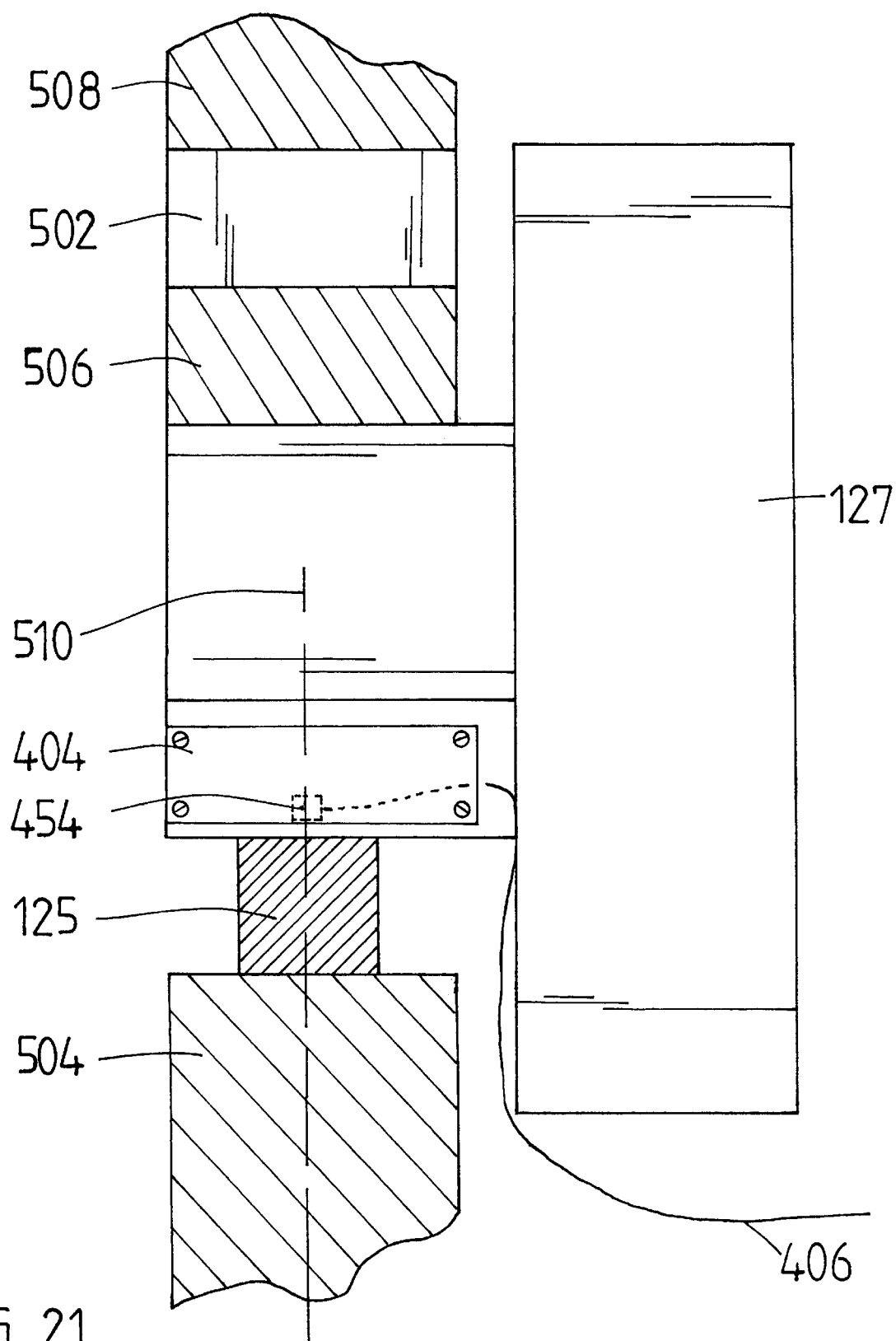
FIG. 21 is a schematic perspective view of an instrumented striker fixtured in a tensile machine equipped with a calibrated load cell for accurate static calibration of the striker load cell output.
Figure 22:
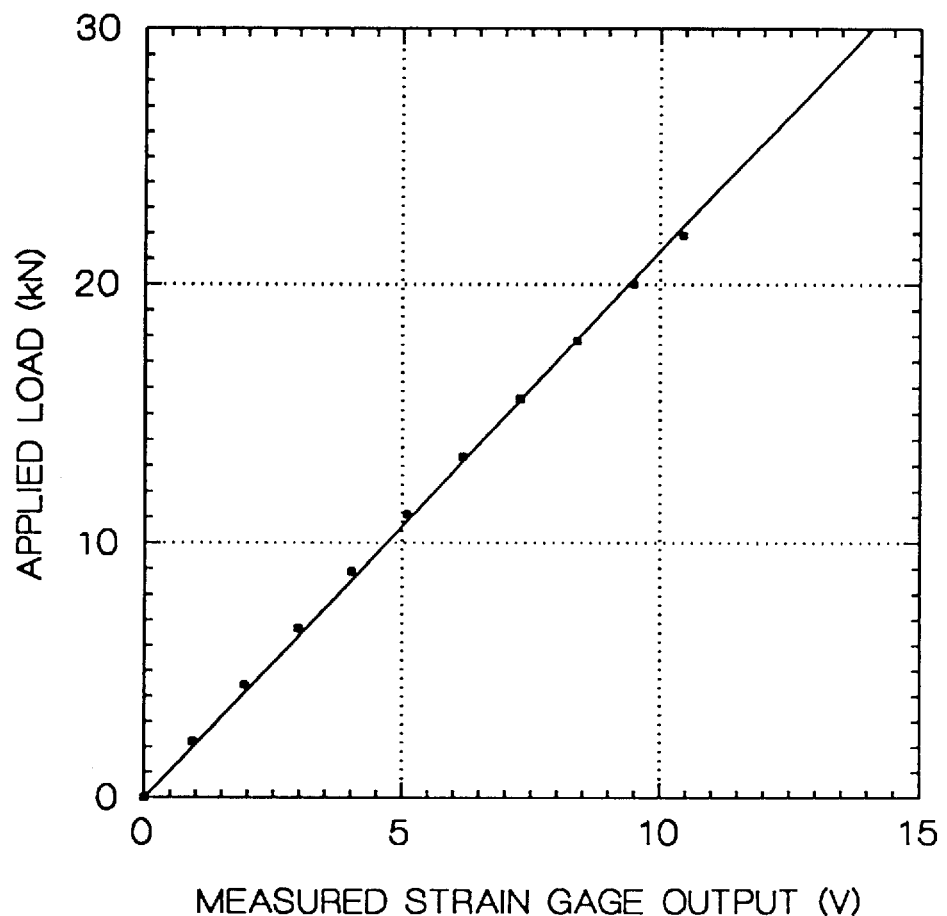
FIG. 22 illustrates typical strain gage calibration data obtained using a calibrated load cell traceable to the National Institute of Standards and Technology (NIST) to provide an applied load which is used to calibrate the instrumented striker measured strain gage output.

In addition to circuit design and optimal stain gage placement on the striker, it is essential that the calibration of instrumented striker be performed correctly to ensure accurate load measurements. Good laboratory practice would include using the actual wires, amplifier, computer boards, and computer in the calibration as in the actual system. However, it has been discovered that the calibration must be performed with a steel block of the exact specimen dimensions at the actual impact location in place against the striker surface during static calibration. The current art is to calibrate with the striker clamped between two flat plates. This invention teaches that the actual load depends strongly on the position of the specimen along the striker surface. Referring to FIG. 21, the calibration may be performed in a tensile test machine (or in a fixture capable of applying loads) equipped with a calibrated load cell. Striker 127 with active strain gages 454 and 456 is placed in tensile machine with specimen centered on center of strike 510. In a pendulum machine, center of strike 510 is the same as center of percussion. The measured load response will change if the centerline of specimen 125 is moved so as to not be coincident with center of strike 510. A rigid plate 504 is attached to the tensile machine to support specimen 125. A rigid plate 506 is attached to tensile machine calibrated load cell 502 to support striker 127 during compressive loading. A rigid plate 508 is attached to load cell 502 and to tensile machine load train to provide support for calibrated load cell 502. Calibration is performed by applying a compressive load to the load train and recording the calibrated load cell output and the striker load cell output at several static loads. More than one static load is preferable so that non-linearity of the striker load cell can be accurately determined. Referring to FIG. 22, a typical striker load cell calibration is illustrated. The tensile machine load cell is used to provide an applied load to the striker and the striker measured strain gage output in volts is recorded. The effects of nonlinearities may reduced by adjusting striker output to match the applied load near the middle of the calibrated load range. As shown in FIG. 22, this approach results in loads which are reasonably approximated by a linear fit. In a preferred embodiment, the conversion of striker measured strain gage output is performed by interpolation between calibration points.

Figure 23:
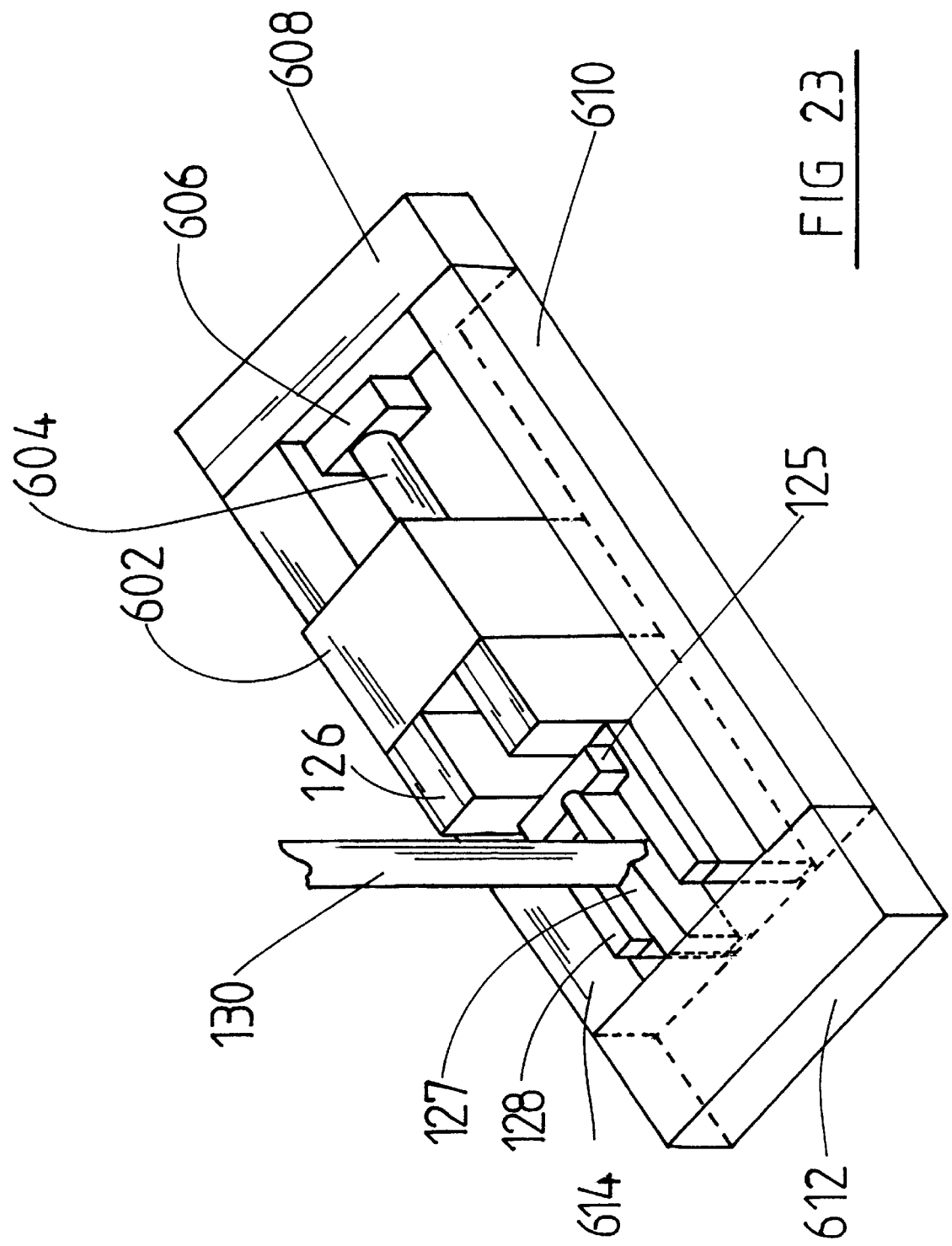
FIG. 23 is a schematic perspective view of an instrumented striker calibration us which enables calibration of the striker load cell while it is in place in a pendulum impact test machine.

While the above calibration procedure is accurate and effective and has been used extensively by the inventor, it requires removal of the instrumented striker from the test machine. ASTM E 23 requires test machine verification after replacing parts that may affect the measured energy. In order provide a means for instrumented striker verification without the need to remove the striker from the test machine, an apparatus and method has been invented. This is not obvious because the geometry of a pendulum impact machine does not readily lend itself to application of static loads. Referring to FIG. 23, an expandable member 602, such as a hydraulic jack, is placed on the back side of anvils 126. A hydraulic piston 604 is connected to a calibrated load cell 606. A force reaction frame, which consists of a top member of force reaction frame 608, a right side member of force reaction frame 610, a bottom member of force reaction frame 612, and a left side member of force reaction frame 614, is assembled such that top member 606 is in contact with calibrated load cell 606 and bottom member 612 is in contact with back surface of striker 127. Hydraulic jack 602 is used to displace hydraulic jack piston 604 so as to apply a force to specimen 125. At various hydraulic jack piston 604 displacements, the load applied to calibrated load cell 606 and to instrumented striker 127 will change to enable calibration of instrumented striker 127 over a desired load range. It is important to note that there are other geometries which will achieve the objective of calibrating an instrumented striker after it has been installed in an impact test machine. An example of an alternative geometric arrangement is to drill and tap the base of the Charpy test machine and attach a load reaction member behind the striker after it has been placed in contact with the specimen. Another approach would be to attach a force reaction member to the specimen supports. However, the preferred embodiment shown in FIG. 23 has the advantage that no special machining or modifications to the test machine are needed and the preferred embodiment ensures that forces are applied to the instrumented striker and calibrated load cell in a substantially co-linear manner.

Best Mode—Summary

1. A method for thermally conditioning a specimen (125) in-situ prior to performing an impact test, comprising the steps of:
   a. positioning said specimen in a test fixture (126,128);
   b. thermally conditioning said specimen by flowing a thermally conditioned fluid over surfaces of said specimen;
   c. impacting said specimen; and
   d. measuring at least one of an absorbed energy, an applied load or a specimen deflection such as absorbed energy, applied load, and/or specimen deflection;
   whereby said specimen will be impact tested with an accurate alignment at a known temperature.
2. A method according to 1 wherein said test fixture is thermally preconditioned.
3. A method according to 1 wherein said test fixture is a Charpy pendulum impact test machine.
4. A method according to 1 wherein said test fixture is a drop tower impact test machine.
5. A method according to 1 wherein said thermally conditioned fluid is air, and/or inert gas, and/or gas, and/or liquid.
6. A method according to 1 wherein said thermally conditioned fluid flow is directed over surfaces (137,138,139, 140) of said specimen which are adjacent to volume of material which undergoes deformation during said impact test which affects fracture behavior.
7. A method according to 1 wherein said thermally conditioned fluid is air which is dehumidified prior to said thermal conditioning.
8. A method according to 1 wherein said specimen is precisely aligned with a notch and/or a precrack centered between test fixture anvils (126) on test fixture supports (128).
9. An apparatus for providing thermal conditioning of a fracture behavior test specimen (125) prior to performing an impact test, comprising:
   a. a pressurized fluid capable of flowing through a duct;
   b. a heater and/or refrigerator capable of thermally conditioning said fluid; and
   c. means for flowing said thermally conditioned fluid over surfaces (137,138,139,140) of said fracture test specimen which is fixtured in an impact test machine prior to impact testing;
   thereby said specimen is impact tested with an accurate alignment at a known temperature.
10. A method for determining conventional Charpy V-notch upper shelf energy of a material using a miniature specimen, comprising the steps of:
    a. impact testing said miniature specimen at a temperature which yields entirely ductile fracture;
    b. measuring total absorbed energy in step a.,
    c. calculating a fracture process volume for a Charpy V-notch specimen and for said miniature specimen;
    d. calculating a ratio of the Charpy V-notch specimen fracture process volume to the miniature specimen fracture process volume;
    e. determining a plastic zone correction factor which relates the miniature specimen fracture process volume to the Charpy specimen fracture process volume; and
    f. calculating substantially equivalent Charpy V-notch upper shelf energy by multiplying energy measured in step b. by the fracture process volume ratio calculated in step d. and multiplying the result by the plastic zone correction factor determined in step e.,
    whereby an upper shelf energy will be determined using miniature specimens which is substantially equivalent to the upper shelf energy which would be obtained by testing conventional Charpy V-notch specimens at a temperature which yields entirely ductile fracture.
11. A method according to 10 wherein said fracture process volume and/or plastic zone correction factor is determined by finite element analysis.
12. A method according to 10 wherein said plastic zone correction factor is determined using characteristic loads.
13. A method for measuring percent shear fracture area of a fracture behavior specimen, comprising the steps of:
    a. capturing a digitized image of said fracture behavior specimen fracture surface on a computer;
    b. outlining brittle fracture region and total fracture region of said fracture surface;
    c. using computer program to calculate the area of said regions of step b.; and
    d. calculating percent shear fracture area and/or percent brittle fracture area using said areas of step d.;
    whereby an accurate and reproducible measurement of the percent shear and/or percent brittle fracture area of a fracture behavior test specimen is made.
14. A method for measuring lateral expansion of a fracture behavior specimen, comprising the steps of:
    a. capturing a digitized image of said fracture behavior specimen fracture surface on a computer;
    b. marking said digitized image of step a. to define the extent to which the lateral expansion has occurred on said fracture behavior specimen; and
    c. measuring the distance between said marks of step b. in a direction which is substantially normal to the direction of crack propagation and substantially in the direction of lateral expansion material flow;
    whereby and accurate and reproducible measurement of the lateral expansion which occurs during fracture is made.
15. A method according to 14 wherein said lateral expansion measurements are made at the two locations on each broken specimen half where lateral expansion occurs.
16. A method according to 15 wherein a total lateral expansion is determined to be a sum of the greater of the two lateral expansion measurements taken from one side of the specimen and the greater the two lateral expansion measurements take from the opposite side of specimen.

17. A method for measuring force during impact testing, comprising the steps of:
   a. attaching active strain gages (454,456) to a striker (127);
   b. locating said active stain gages of step a. well within one stress wavelength of striking surface; and
   c. completing load cell circuit by locating balancing resistors (458,459) away from striker where stress waves from impact test cannot be sensed.

18. A method according to 17 wherein said active strain gages are attached on said striker substantially along center of percussion.

19. A method according to 17 wherein said active strain gages and said balancing resistors form a Wheatstone bridge circuit.

20. A method according to 17 wherein said active strain gages are protected by covers (404) mounted on striker.

21. A method for calibrating an instrumented striker, comprising the steps of:
   a. positioning said instrumented striker between two flat plates (504,506) in a tensile machine load train which contains a calibrated load cell (606);
   b. placing a specimen of substantially same dimensions as will be impact tested using said instrumented striker between instrumented striker and one of said flat plates of step a.;
   c. aligning said instrumented striker and said specimen of step b. such that specimen is in contact with said instrumented striker in said tensile machine load train in substantially the same position and orientation as in an impact test machine which will be used for impact testing;
   d. applying static loads to said instrumented striker and said calibrated load cell to determine the relationship between instrumented striker voltage output and applied force.

22. A method for calibrating an instrumented striker which is installed in an impact test machine, comprising the steps of:
   a. placing a specimen of substantially same dimensions as specimens to be impact tested on said impact test machine specimen supports against anvils;
   b. positioning said test machine striker in contact with said specimen of step a.;
   c. placing an expandable member (602) against test machine anvils;
   d. surrounding said instrumented striker and said expandable member with a force reaction frame (608,610,612, 614) which contains a calibrated load cell (606);
   e. applying displacements using said expandable member such that said force reaction frame applies a load to instrumented striker and to said calibrated load cell;
   f. recording at least one output voltage from said instrumented striker and from said calibrated load cell to relate instrumented striker output voltage to applied force.

23. An apparatus for calibrating an instrumented striker which is installed in an impact test machine, comprising:
   a. a calibrated load cell (606) and an expandable member (602);
   b. a force reaction frame (608,610,612,614) of sufficient size to surround said instrumented striker, said calibrated load cell, and said expandable member;
   c. means for applying displacements using said expandable member such that a load is applied simultaneously to said calibrated load cell and said instrumented striker.

The following references are incorporated herein:
(1) Manahan et al., U.S. Pat. No. 4,567,774, "Determining Mechanical Behavior of Solid Materials Using Miniature Specimens", Feb. 4, 1986
(2) Manahan, M. P., Sr., U.S. Pat. No. 4,864,867, "Determining Fracture Mode Transition Behavior of Solid Materials Using Miniature Specimens", Sep. 12, 1989
(3) Manahan, M. P., Sr., U.S. Pat. No. 5,165,287, "Determining Fracture Mode Transition Behavior of Solid Materials Using Miniature Specimens", Nov. 24, 1992
(4) Manahan, M. P., Sr., "Miniaturized Charpy Test Optimization for Applications in the Power Industry", Research Report EP 92-38, Final Report, Jun. 21, 1995
(5) ASTM Designation: E 23-93a, "Standard Test Methods for Notched Bar Impact Testing of Metallic Materials"
(6) Nanstad, R. K., et al, "Influence of Thermal Conditioning Media on Charpy Specimen Test Temperature", ASTM STP 1072, 1990
(7) ASTM Designation: EYY-96, "Draft Standard Method for Charpy V-Notch and Miniaturized Charpy V-Notch Impact Tests on Metallic Materials"
(8) Lucas, G. E., Odette, G. R., Sheckherd, J. W., McConnell, P., and Perrin, J., "Subsized Bend and Charpy V-Notch Specimens for Irradiated Testing", The Use of Small-Scale Specimens for Testing Irradiated Material, ASTM STP 888, W. R. Corwin and G. E. Lucas, Eds., American Society for Testing and Materials, Philadelphia, 1986, pp. 305–324.
(9) Corwin, W. R. and Hougland, A. M., "Effect of Specimen Size and Material Condition on the Charpy Impact Properties of 9Cr-1Mo-V-Nb Steel", The Use of Small-Scale Specimens for Testing Irradiated Material, ASTM STP 888, W. R. Corwin and G. E. Lucas, Eds., American Society for Testing and Materials, Philadelphia, 1986, pp. 325–338.
(10) Kumar, A. S., Louden, B. S., Garner, F. A., and Hamilton, M. L., "Recent Improvements in Size Effects Correlations for DBTT and Upper Shelf Energy of Ferritic Steels", Small Specimen Test Techniques Applied to Nuclear Reactor Vessel Thermal Annealing and Plant Life Extension, ASTM STP 1204, W. R. Corwin, F. M. Haggag, and W. L. Server, Eds., American Society for Testing and Materials, Philadelphia, 193, pp. 47–61.
(11) Manahan, M. P. and Charles, C., "A Generalized Methodology for Obtaining Quantitative Charpy Data From Test Specimens of Nonstandard Dimensions", *Nuclear Technology.* Vol. 90, May 1990.

I claim:

1. A method for thermally conditioning a specimen in-situ prior to performing an impact test, comprising the steps of:
   a. positioning said specimen in a test fixture;
   b. thermally conditioning said specimen in said test fixture by flowing a thermally conditioned fluid over surfaces of said specimen which are adjacent to volume of material which undergoes deformation during said impact test which affects fracture behavior;
   c. impacting said specimen; and
   d. measuring at least one key variable in step c.;
whereby said specimen will be impact tested at a known temperature.

2. A method according to claim 1 wherein said test fixture is thermally preconditioned.

3. A method according to claim 1 wherein said test fixture is a Charpy pendulum impact test machine.

4. A method according to claim 1 wherein said test fixture is a drop tower impact test machine.

5. A method according to claim 1 wherein said thermally conditioned fluid is gas or liquid, or both gas and liquid.

6. A method according to claim 1 wherein said thermally conditioned fluid is air which is dehumidified prior to said thermal conditioning.

7. A method according to claim 1 wherein said specimen is precisely aligned with a notch, a precrack, or both a notch and a precrack centered between test fixture anvils on test fixture supports.

8. An apparatus for providing thermal conditioning of a fracture behavior test specimen prior to performing an impact test, comprising:

a. a pressurized fluid capable of flowing through a duct;

b. a heater, a refrigerator, or both capable of thermally conditioning said fluid; and c. means for flowing said thermally conditioned fluid over surfaces of said fracture test specimen which are adjacent to volume of material which undergoes deformation during said impact test which affects fracture behavior while said specimen is fixtured in an impact test machine prior to impact testing;

whereby said specimen is impact tested at a known temperature.

* * * * *